United States Patent [19]

Pettit et al.

[11] Patent Number: 4,978,744

[45] Date of Patent: Dec. 18, 1990

[54] SYNTHESIS OF DOLASTATIN 10

[75] Inventors: George R. Pettit, Paradise Valley; Sheo B. Singh, Tempe, both of Ariz.

[73] Assignee: Arizona Board of Regents, Tempe, Ariz.

[21] Appl. No.: 304,572

[22] Filed: Jan. 27, 1989

[51] Int. Cl.[5] .......................... C07K 5/10; C07K 7/06
[52] U.S. Cl. ..................................................... 530/330
[58] Field of Search .......................... 530/330; 514/17

[56] References Cited

U.S. PATENT DOCUMENTS 4,414,205 11/1983 Pettit ...................................... 514/17
4,486,414 12/1984 Pettit ...................................... 424/95

OTHER PUBLICATIONS

The Isolation and Structure of a Remarkable Marine Animal Antineoplastic Constituent: Dolastatin 10[1a], Pettit et al., JACS vol. 109, No. 22, (1987).

*Primary Examiner*—Lester L. Lee
*Attorney, Agent, or Firm*—Richard R. Mybeck

[57] ABSTRACT

A complicated but extremely important scheme of synthesis has been developed for synthesizing, dolaisoleuine, dolaproine, dolaphenine and dolavaline from readily available starting materials such as Z-(S,S)isoleucine, S-phenylalaline, S-phenylalaninol, S-prolinol, S-mandelate, and S-valine. The requisite amino acids have been combined using several peptide coupling procedures to create pharmaceutically pure dolastatin 10.

24 Claims, 2 Drawing Sheets

SYNTHESIS OF DOLASTATIN 10

INTRODUCTION

The present invention relates generally to the structural determination and the total chemical synthesis of natural (—)-dolastatin 10. Ever since dolastatin 10 was extracted by G. R. Pettit from Indian Ocean sea hare Dolabella, isolated, and found to possess cell growth inhibitory properties, the synthesis of the substance has posed a major dilemma. The present invention represents the ultimate resolution of that dilemma.

Partial funding of this project was obtained from NCI Grant CA-16049-10-12 and several private foundations.

BACKGROUND OF THE INVENTION

Dolastatin 10 was first isolated and elucidated by Dr. George R. Pettit and his associates at the Cancer Research Institute at Arizona State University and was found to possess potent cell growth inhibitory powers. (In 1987 the isolation of dolastatin 10 was reported as the most potent (i.e., lowest in vivo dose) antineoplastic substance known to date by G. R. Pettit and his associates (J.Am. Chem. Soc., 1987, 109, 7581–82). However, the vast number of Dolabella needed to provide sufficient Dolastatin 10 to meet the projected public need effectively prevented this remarkable substance from ever being considered for commercial production. Further, the inability to tightly replicate the natural substance from lot to lot because of the entrainment of even slight amounts of unidentifiable impurities in the extracted product created problems which prevented the natural substance from meeting the strict uniformity required as a condition precedent to the approval of the introduction of a new drug product to the market place by the Food, Drug and Cosmetic Administration and corresponding regulatory agencies in other countries.

Because of the very few milligrams of amorphous dolastatin 10 available for structure determination combined with the chiral complexity (nine assymetric centers), the absolute configuration of dolastatin 10 could not be ascertained at that time. Indeed the most attractive solution to both the stereochemical and the preclinical supply problems associated with dolastatin 10 resides in the development of an effective synthesis of the natural isomer from among five hundred twelve possibilities corresponding to the one-dimensional structure.

Thus, the need to develop an economically viable and truly replicable synthetic procedure for producing substantially pure Dolastatin 10 in large quantities is the principal object of the present invention.

BRIEF SUMMARY OF THE INVENTION

Synthesis of dolastatin 10 is accomplished by a series of strategic procedures which have been developed and which include, inter alia, the reaction of N-Boc-S-dolaphenine ("Doe") with trifluoroacetic acid (Tfa) to form the trifluoroacetate salt of dolaphenine which in turn is reacted with Boc-(2S,2'R,3'R)-dolaproine ("Dap") to form dipeptide Boc-(2s,2'R,3'R)-Dap-S-Doe which is then reacted with Tfa to form a dipeptide Tfa salt.

S-Dov-S-Val-(3R,4S,5S)-Dil-OBu$^t$ is reacted with Tfa to form a tripeptide Tfa salt which is admixed with the dipeptide Tfa salt created by the first reaction and triethylamine and diethylphosphorocyanidate DEPC is added thereto to provide as the reaction product thereof, crude dolastatin 10, which when purified, is of acceptable pharmaceutical grade.

In the course of the work resulting in the successful synthesis of dolastatin 10, the structure of which is shown in FIG. 1, it was necessary to create three new synthetic amino acids respectively denominated "dolaisoleuine" (abbreviated therein as "Dil") which is shown in FIG. 2; "dolaproine" (abbreviated "Dap") which is shown in FIG. 3; and "dolaphenine" (abbreviated "Doe") which is shown in FIG. 4.

The preparation of the tert butyl ester of dolaisoleuine is described hereafter as Example 6. The amino acid Dil is obtainable by deblocking or clearing the tert butyl ester from that product with trifluoroacetic acid.

The preparation of N-Boc-(2S,2'R,3'R)-dolaproine is described in Example 15. The amino acid Dap is also obtained by deblocking the Boc-group therefrom with trifluoroacetic acid.

The preparation of N-Boc-2(3),4(5)-tetrahydrodolaphenine is described in Example 20. The amino acid Doe can be similarly obtained by reacting the tetrahydrodolaphine with trifluoroacetic acid.

Accordingly, a principal object of the present invention is to provide an effective and commercially viable process for synthesizing dolastatin 10.

A further object of the present invention is to provide a process for synthesizing dolastatin 10 which can be readily replicated to provide a continual and uniform product supply.

These and still further objects as shall hereinafter appear are fulfilled by the present invention in a remarkably unexpected fashion as can be readily discerned from a careful consideration of the following detailed description of exemplary embodiments thereof, especially when considered in conjunction with the accompanying drawings.

DESCRIPTION OF PREFERRED EMBODIMENTS

Figure 1:
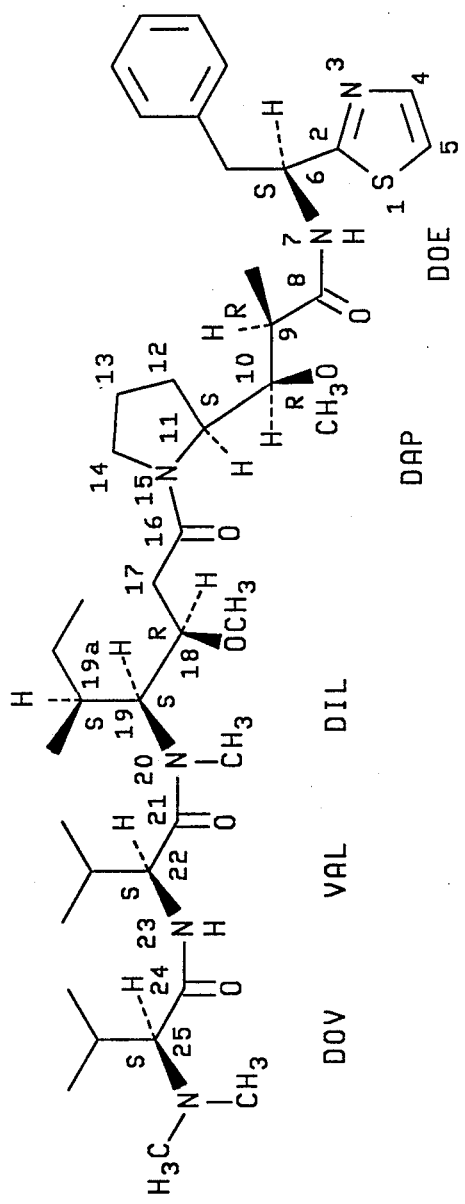
Figure 4:
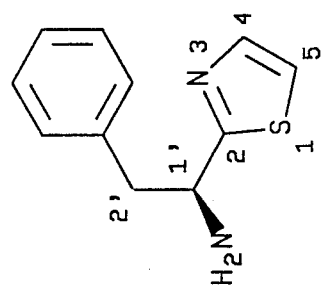
Figure 3:
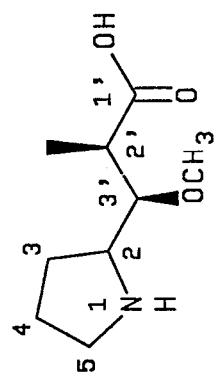
Figure 2:
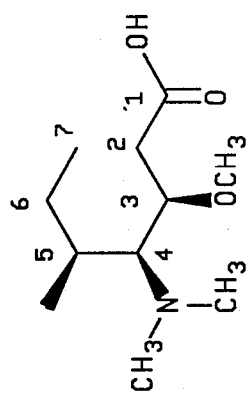

This disclosure is predicated upon our discovery of the absolute configuration and total synthesis of natural (—)- dolastatin 10 which has the following structure.

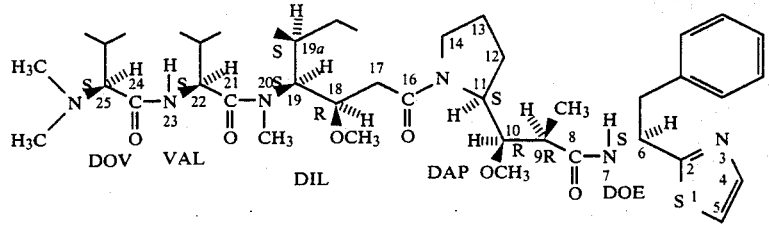

Our earlier work with Dolastatin 3 suggested the amino acid biosynthetic precursors of dolastatin 10 would likely carry the L-(S notation thereupon) and Ile the (S,S)-configuration. Furthermore, a synthetic specimen of S-Dov-S-Val (DCCI-HBT coupling, mp 96°–7° C. from acetone-hexane $[\alpha]_D^{30} -17°$ (c=3.6, CHCl$_3$) corresponded exactly to a dolastatin 10 acid hydrolysis product when a derivative of both were co-injected and chromatographed on a Chirasil Val gas chromatographic column. With these clues in mind synthesis of dolastatin 10 was initiated. Careful 2D-NMR (400 MHz) comparative interpretations of the natural product with the diasterioisomeric dolaisoleuine ("Dil") and dolaproine ("Dap") synthetic intermediates were employed to select the most probable chiral isomers.

Synthesis of the necessary Dil component (3R,4S,5S)-Dil-OBu$^t$.HCl (mp 145°–7° C. from ether, $[\alpha]_D^{30}$ 7.3° (c=4.5, CHCl$_3$)) was realized by methylating (NaH, CH$_3$I) Z-(s,S)-isoleucine followed by reduction (dibroane-THF) to N-Z-N-Me-(S,S)-isoleucinol (95% overall, oil, $[\alpha]_D^{30} -11.3°$ (c=5.6, CHCl$_3$)), oxidation (DMSO-SO$_3$-Py) to the aldehyde (78%, $[\alpha]_D^{30} -66°$ (c=4.36, CHCl$_3$)), aldol condensation (at −78°, 45 minutes, in THF) with the lithium enolate (lithium diisopropylamide) from t-butyl acetate to yield (87% total, following silica gel column chromatography, hexane-acetone) the (3S,4S,5S)-(23% yield, viscous oil, $[\alpha]_D^{35} -37.8°$ (c=5.0, CHCl$_3$) and (3R,4S,5S)- (33% yield, viscous oil, $[\alpha]_D^{35} -3.10$ (c=4.25, CHCl$_3$). The 3R-isomer was methylated (diazomethane-boran trifluoride etherate) and the product (67% yield, oil, $[\alpha]_D^{35} -15.5°$ (c=4.9, CHCl$_3$) subjected to hydrogenolysis (63% yield of (3R,4S,5S)-Dil-OBu$^t$.HCl using 3:1 ethyl acetate-methanol, 1 day, 5% Pd/C, H$_2$, then HCl at −60° in ether). The latter reaction also afforded (4R-methoxy-5S-(1'S-methyl)propyl-2-pyrrolidinone) (29%, viscous oil, $[\alpha]_D^{30} -6°$ (c=0.9, CHCl$_3$) required for $^1$H-NMR analysis and in turn confirm stereochemical assignments for the Dil series. Lactam formation was almost completely eliminated by a short (2 hour) hydrogenolysis period.

In the course of this work, it became imperative that the absolute configuration of dolaproine be determined and a practical stereoselective total synthesis of this more complex (3 chiral center) amino acid be developed if a total synthesis of dolastatin-10 is to be evolved.

Based on our difficultly earned knowledge of *Dolabella auricularia* peptides, the premise was established that dolaproine was derived from S-proline and that by detailed high field (400 MHz) NMR comparisons between dolastatin 10 and synthetic dolaproines, the correct chiral assignments for dolastatin 10 could be ascertained.

Of the synthetic routes explored, an aldol condensation approach was most successful. Protection of the amino function of S-prolinol with the Boc group followed by modified (DMSO-trifluoroacetic anhydride) Swern or Parikh-Doering (DMSO-SO$_3$-Py) oxidation to Boc-S-prolinal [oil, $[\alpha]_D -96°$ (c=1.19, CHCl$_3$] proceeded well (75% overall). Aldol condensation (at −95° C. for 2 hours) of this aldehyde with the chiral enolate derived (lithium diisopropylamide) from 2S-propionyloxy-1, 1, 2-triphenylethanol [mp 215°–16° C. from acetone-hexane, $[\alpha]_D^{30} -203.5°$ (c=1.44, CHCl$_3$)] in tetrahydrofuran containing freshly prepared magnesium bromide (to enhance stereoselectivity) afforded the nearly correct 2S, 2'S, 3'R)-isomer (glistening crystals from acetone-hexane mp 128°–30°, $[\alpha]_D^{30} -146.9°$ (c=2.45, CHCl$_3$) as major product (47% yield by silica gel column chromatographic separation). By HPLC analysis (RP-8 with acetonitrilewater, 50–100%), the four possible diastereoisomers were present in the ratio 63:7:15:15. When the aldol reaction was conducted at the warmer −78° C., stereoselectivity was reduced leading to a 45:15:20:20 ratio of isomers. The diastereoisomer corresponding to dolaproine was not easily separated from the others. So as described below simple 2'-position epimerization of the major isomer proved convenient and overcame this hurdle. The absolute configuration of this isomer was unequivocally established (see FIG. 1) by x-ray crystal structure determination of the easily formed (by hydrogenolysis, esterification, trifluoroacetic acid and potassium carbonate) 4R-hydroxy-3S-methyl-5S-pyrrolizidin-2-one (mp 121°–2° from acetone-cyclohexane $[\alpha]_D^{30} -115°$ (c=1.85, CHCl$_3$).

A crystal (0.33×0.2×0.33 mm, from acetonecyclohexane) of 4R-hydroxy-3S-methyl-5S-pyrrolizidin-2-one was subjected to data collection with an Enraf-Nonius CAD-4 diffractometer. The crystal was assigned the monoclinic P21 space group density 1.248 (CCl$_4$) and cell volume 412.57 Å$^3$ (a=5.4204(5) Å, b=10.5563(8) Å, c=7.2380(6) Å, b=95.007(7). Measurement (room temperature) of all unique reflections with 2°⊖<130° was accomplished (w-20 technique) with graphite-monochromated CuK radiation (1.54178 A). After merging equivalent reflections, removal of systematic absences, and rejection of "unobserved" reflections, {[Fo]<3[Fo]), a data set consisting of 1640 unique reflections was obtained and used in the subsequent refinement processes. Direct methods structure solution was readily accomplished with MULTAN-80, (See: Main, P. *A System of Computer Programs for the Automatic Solution of Crystal Structures from X-Ray Diffraction Date,* University of York, England, 1980). All refinement calculations were completed by using the "CRYSTALS" computing package, (See: "CRYSTALS" by Watkin et al, 1985, Chemical Crystallography Laboratory, University of Oxford, Oxford, UK.) Full-matrix least-squares anisotropic refinement of the nonhydrogen contents of the unit cell was performed. All H atoms were placed at idealized positions, assigned isotropic thermal parameters, but not refined. The model for 4R-hydroxy-3S-methyl-5S-pyrrolizidin-2-one converged to residuals R=0.053 and Rw=0.058 (anamalous dispersion corrections made and extinction parameter included in the refinement) for 1643 reflections. Based upon the known absolute stereochemistry of C-5, the complete absolute stereochemistry of all chiral centers was assigned the as follows: 3S,4R,5S. Thus the dolaproine isomer from which the 4R-hydroxy-3S-methyl-5S-pyrrolizidin-2-one was prepared must have absolute configuration as 2S,2'S,3'R.

Treatment of the major aldol product with boron trifluoride etherate-diazomethane or better by trimethyloxonium tetrafluoroborate in methylene chloride gave the 3'R-methyl ether derivative (crystals from acetone-hexane, mp 130°–2°, $[\alpha]_D^{30} -169.7°$ (c=4.15, CHCl$_3$). Epimerization of the 2'S-methyl group of the propionate necessitated rather specific conditions, namely short contact (2–5 min and termination with sat. citric acid) with potassium tert-butoxide in THF at −20° C. to provide (57%) the 2'R-methyl epimer (mp 130°–2° from acetone-hexane $[\alpha]_D^{30} -154.6°$ (c=0.01, CHCl$_3$). Hydrogenolysis (Pd/C) of the benzyl ester led to N-Boc-(2S,2'R,3'R)-dolaproine (mp 138°–142° C. from acetone-hexane, $[\alpha]_D^{30} -40°$ (c=3.0, CH$_3$OH) a key intermediate in the successful total synthesis of dolastatin 10. Mild treatment with trifluoroacetic acid led to natural (2S, 2'R, 3'R)-dolaproine as trifluoroacetate salt (mp 215°–220° from methanol-ether [α]$_D^{30}$ −10° (c, 0.5, CH$_3$OH).

Preparation of dolaphenine followed the probable biosynthetic route we outlined in 1982 for thiazole amino acids (See: Pettit et al, J. Am. Chem. Soc., 1982, 104, 1905 at fn 11). Conversion of Boc-S-Phe to the corresponding N-Boc-S-phenylalaninal (powder, mp 67°–9°, [α]$_D^{30}$ −37.5° (c=1.0, CHCl$_3$) was performed as above (Dil sequence). Condensation with 2-aminoethanothiol and dehydrogenation (in dioxane, RT, through a column of battery grade manganese dioxide) of the thiazolidines (98% yield) afforded (14%) N-Boc-S-Doe (crystals from acetone-hexane, mp 106°–7° [α]$_D^{30}$ −23.2°, (c=0.6, CHCl$_3$)

With some use of techniques from our recent synthesis of dolastatin 3, pivaloyl anhydride coupling for the N-methyl amino acid (Dil), and proceeding (See: Scheme 1 in FIG. 5) via (N-Z-S-Val-N-methyl-3R,4S,5S-Dil-OBu$^t$, 80%, oil, [α]$_D^{30}$ −58° (c=0.5, CHCl$_3$), S-Dov-S-Val-N-methyl-3R, 4S,5S-Dil-OBu$^t$, (83%, crystals from acetone-hexane, mp 104°–6° [α]$_D^{28}$ −50° (c=1.6, CH$_3$OH) and N-Boc-2S,2'R,3'R-Dap-Doe (50%, viscous oil) natural (−)-dolastatin 10 was obtained (74%, following purification on SEPHADEX® LH-20, 2:7.5:2.5 hexane-dichloromethane-methanol, and silica gel, 1–5% gradient, dichloromethane-methanol) as an amorphous powder (mp 102°–6° from acetone hexane, [α]$_D^{27}$ −57° (c=0.026, CH$_3$OH) identical by HPLC, TLC, $^{13}$-NMR and, most importantly, by 400 MHz $^1$H-NMR (in CH$_2$Cl$_2$ solution) with an authentic specimen. Synthetic dolastatin 10 also exhibited the same level (ED$_{50}$10$^{-4}$ μg/mL) of activity against the P388 lymphocytic leukemia as routinely obtained with the natural product.

More particularly, in the synthesis of dolastatin 10, twenty-eight discrete steps or procedures are involved in sequence to effectuate the necessary chemical changes (omitting the purely physical steps such as drying, filtration, heating and the like).

Of these twenty-eight procedures, eight are considered critical and unique and will be specifically addressed here. The others, albeit important to the overall scheme to produce the desired result, involve the more mundane aspects of polypeptide synthesis such as bond formation, and the protecting and deprotecting of reactive groups, and the like.

One involves placing the cooled and well-stirred solution of tert-butyl-(3R,4S,5S)-3-hydroxy-4-(N-Z, N-methyl)-Amino-5-methyl-heptanoate under argon in dichloromethane and adding boron trifluoride etherate thereto. About 30 minutes later, an anhydrous solution of diazomethane (large excess prepared from Diazald) in dichloromethane is added thereto. After about one hour, the polymethylene side-products are removed by filtration. The filtrate is then concentrated and the solution is chromatographed (flash silica gel) and the column eluted with hexane-acetane (97:3) to provide the methylether as a pure oil. (Refer to Example 6, infra, for more detail.)

A second critical procedure involves the methylether (tert-butyl (3R, 4S, 5S)-3-methoxy-4-(N-Z-N-methyl-)amino-5-methyl-heptanoate) produced in by the above identified procedures ethyl acetate-methanol (3:1) and adding 5% Pd/C catalyst thereto. The mixture is then hydrogenated overnight at ambient temperature and pressure. The catalyst is removed by filtration and the filtrate is evaporated to dryness. This dry filtrate is then dissolved in ether, cooled to −60° C. and an ethereal solution of hydrogen chloride is added under anhydrous conditions. The hydrochloride salt precipitates immediately and the excess hydrogen chloride is removed by passing argon into the mixture. The amorphous tert-butyl (3R,4S,5S)-3-methoxy-4-(N-methyl)-amino-5-methyl heptanoate hydrochloride (Dil-OBu$^t$ HCl) is collected by filtration and the filtrate is chromatographed on a column of silica-gel and eluted with hexane-acetone (4:1) to yield the corresponding lactam 4R-methoxy-5S-(1'S-methyl) propyl-2-pyrrolidinone as a gum. (Refer to Example 7, infra, for greater detail.)

The third critical procedure involves the formation of N-Boc-2S-3'-[2''-Ethoxy-4''-Hydroxy-1'',1'',2''-Triphenyl) 2'S-Methyl-3'R-Hydroxy-Propionate]-Pyrrolidine using a propionate ester which was previously prepared. Specifically, a suspension of the propionate ester (prepared according to Example 10, infra) is added to a solution of lithiumdiisopropyl amide. The reaction mixture was allowed to warm up to room temperature and two hours later, the yellow solution was cooled to −95° C. Next, freshly synthesized magnesium bromide is added followed (1 hour interval) by a solution of Boc-S-prolinal (prepared according to Example 9, infra). After two hours, the reaction is terminated by the addition of saturated aqueous ammonium chloride. The mixture is then allowed to warm to 0° C. and ether is added. The ethereal solution is then washed, dried, and the solvent evaporated to give a glassy solid mixture. The mixture is then preadsorbed on silica gel, chromatographed, and eluted with hexane-acetone to provide some unreacted ester, diasteromeric mixture of (2'R,3'R), (2'S,3'S), and (2''R,3'R), and as the major product, the 2'S,3'R isomer. The 2'S,3'R-isomer is isolated as an amorphous powder from acetone-hexane, mp 128°–130° C.

The fourth critical procedure involves the production of N-Boc-2S-3'-[2''-Ethoxy(1''-Hydroxy-1'',1'',2''-Triphenyl) 2'S-Methyl-3'R- Methoxy-Propionate]Pyrrolidine. Specifically, this procedure involves the methylation of the 2'R,3'R-isomer (produced according to Example 11, infra) in dichloromethane with boron trifluoride etherate and diazomethane in anhydrous dichloromethane. The resulting product is isolated (using the procedures described in Example 6, infra) and eluted with hexane-acetone to yield the methyl ether identified above.

The same result is obtained when the alcohol (produced by Example 10, infra) is added in dichloromethane to a stirred suspension of trimethyloxonium tetrafluoroborate in dichloromethane at room temperature. Proton sponge (2.0 g, 9.4 mmol) is then added to the mixture which is stirred at room temperature for 16 hours. The solvent is thereafter removed to provide a yellow solid which is preadsorbed on silica gel, subjected to flash column chromatography, and eluted with 9:1 hexane-acetone to provide the pure methyl ether identified above.

The fifth critical procedure involves the production of N-Boc-2S-3'-[2''Ethoxy(1''-Hydroxy-1'',1'',2''-Triphenyl) 2'R-Methyl-3'R-Methoxy-Propionate]-Pyrrolidine by adding a solution of potassium tert-butoxide in THF to the (2'S,3'R)-ester (produced according to Example 12, infra) in THF with stirring. After warming to −15° C., the epimerization of the solution was stopped with saturated aqueous citric acid, diluted with the same solution, and extracted with dichloromethane (3×10 ml). The combined extract was washed with water, dried and the solvent removed therefrom to provide a yellow oil (0.16 g). Flash chromatography on silica gel (19:1) hexane-acetone, eluant) afforded as a clear oil the 2'R,3'R-epimer of the desired pyrrolidine.

The sixth critical procedure involves the formation of 2-(1'S-Boc-Amino-2'-Phenyl-ethyl)-Thiazole; (N-Boc-S-Dolaphenine); (Boc-S-Doe). The procedure involves adding phenylalanyl thiazolidine (prepared according to Example 20, infra) in benzene to a suspension of battery grade (Type M) manganese dioxide in anhydrous benzene. The mixture is stirred under argon at 55° C. for 24 hours, whereupon additional manganese dioxide is added and the stirring is continued for another 48 hours. The resulting solution is filtered through a narrow bed of silica gel and sequentially eluted with benzene ethyl acetate, chloroform, and chloroform-acetone (1:1). The combined eluant is then evaporated to dryness and the resulting residue is flash chromatographed to yield the aforesaid thiazole, (Boc-S-Doe), an amorphous solid.

Alternatively, but equally significant, the thiazole Boc-S-Doe can be routinely prepared using the following procedure. Activated manganese dioxide is mixed with dry dioxane and the resulting slurry is added to a dry glass column (7.5 mm I.D.). The column is then lightly packed by eluting with dioxane under a positive pressure of nitrogen. The thiazolidine 2-(N-Boc-1'S-Amino-2'Phenyl-ethyl)-2(R,S)-Thiazolidine (prepared according to Example 20, infra) in dry dioxane is allowed to flow through the column over a four hour contact time. After removing an initial fraction which contains side-products, the next fraction provides Boc-S-Doe.

The seventh critical procedure involves the production of N-Z-(S)-Val-(3R, 4S, 5S)-Dil-OBu$^t$ by adding with stirring to a cooled −23° C. solution of N-Z-S-valine in anhydrous chloroform, N-methyl morpholine and, ten minutes later, pivaloyl chloride. The mixture is stirred at −23° C. for three hours and solid (3R,4S,5S)-Dil-OBu$^t$.HCl (50 mg, 0.17 mmol) and N-methyl morpholine (0.02 ml, 0.18 mmol) are added. This new mixture is then stirred at −23° C. for another two hours and then concentrated by sweeping the mixture with argon at room temperature. The stirring is continued for three days and chloroform is added. Thereafter, the solution is sequentially washed with saturated aqueous citric acid, water, aqueous sodium bicarbonate, and water, dried and solvent evaporated. Flash chromatography (silica gel column) using hexane-acteone (9:1) as eluant yielded the dipeptide N-Z-S-Val-(3R,4S,5S)-Dil-OBu$^t$ (65 mg, 80%) as a viscous oil.

The eighth and final critical procedure involves the production of S-Dov-S-Val-(3R,4S,5S)-Dil-OBu$^t$. In this production, a solution of dolavaline in pyridine is cooled to 0° C. and pentafluorophenol trifluoroacetate is added under argon. The solution is then stirred at room temperature for 30 minutes, ethyl acetate is added thereto, and the resulting organic phase is washed sequentially with 10% aqueous sodium bicarbonate and water; dried and solvent evaporated to an oil. The oily active ester is then eluted with hexane-acetone (99:1) to give dolavaline pentafluorophenol ester (1.2 g, 77%) (Dov-Pfp).

To a solution of Z-(S)-Val-(3R,4S,5S)-Dil-OBu$^t$ (prepared according to Example 24, infra) and Dov-Pfp, (prepared as above) in anhydrous dioxane, is added 10% Pd/C catalyst. The mixture is saturated with hydrogen overnight under anhydrous conditions at ambient temperature and pressure. The catalyst is removed by filtration and the solvent evaporated. The residue is dissolved in benzene and treated with trifluoroacetic anhydride at 0° C. under argon. The resulting solution is then stirred for ten minutes (to form pentafluorophenol trifluoroacetate) and the solvent is removed therefrom leaving a residue which is chromatographed on a column of SEPHADEX ® LH-20 and thereafter submitted to flash chromatography to give tripeptide S-Dov-S-Val(3R,4S,5S)-Dil-OBu$^t$ as a powder.

The total synthetic solutions to the dolastatin 10 stereochemical and availability problems provided by the present invention will now greatly accelerate preclinical development, synthesis of potentially useful structural and chiral modifications, and a broad assessment of biological properties of dolastatin 10.

To better understand the present invention and not by way of limitation, the following examples are presented.

EXAMPLE 1

Experimental Parameters

The amino acids and derivatives Z-(S,S)-isoleucine, S-valine, Z-S-Valine, S-phenylalaninol, and S-phenylalanine were obtained from Sigma and (S)-prolinol from Aldrich Chemical Co. All other reagents were obtained from Sigma-Aldrich or Lancaster synthesis. Solvents were redistilled and solvent extracts of aqueous solutions were dried over anhydrous sodium sulfate. Evaporation of solvents was performed under reduced pressure on a Buchi rotary evaporator.

As used herein, "Ether" refers to diethyl ether, "THF" to tetrahydrofuran; "DMF" to dimethylformamide; and "DMSO" to dimethylsulfoxide. THF was distilled from lithium aluminum hydride prior to use. Proton sponge supplied by Aldrich Chemical Company corresponds to [1,8-bis(dimethyl-amino)naphthalene, N,N,N',N'-tetramethyl-1,8-naphthalene-diamine]. Battery grade manganese dioxide was obtained from Chemetals, Maryland. ANALTECH ® silica gel GF (0.25 mm) plates were used for thin layer chromatography (TLC) and developed with either 3% ceric sulfate in 3N sulfuric acid spray and/or iodine vapor. Stationary phases used for gravity or flash column chromatography were E. Merck (Darmstadt) silica gel (70–230; for gravity column and 40–63; for flash column). Whatman silica gel LPS-1 (13–24) or SEPHADEX ® LH-20 (Pharmacia Fine Chemicals AB, Uppsala, Sweden).

Melting points were observed with a Kofler-type hot stage apparatus. Optical rotation measurements were recorded using a Perkin-Elmer 241 polarimeter. The Ultraviolet spectra were obtained in methanol solution with a Hewlett-Packard 8450A UV/vis spectrophotometer. A Nicolett MX-1 FT spectrophotometer was employed for infrared measurements. Tetramethylsilane, residual chloroform (7.256 ppm) or dichloromethane (5.32 ppm) was used as an internal reference in all nuclear magnetic resonance measurements determined with Bruker AM 400 ($^1$H, $^{13}$C), or WH 90 ($^1$H) instruments and chemical shifts are recorded in ppm (K). Deuteriochloroform was used as NMR solvent unless otherwise mentioned. The HREI and SP-SIMS (FAB) mass spectra were recorded with a Kratos MS 50 instrument in the NSF regional mass spectrometry facility at the University of Nebraska. Elemental analyses were determined by Dr. A. W. Spang (Spang Microanalytical Laboratory, Eagle Harbor, Mich.).

EXAMPLE 2

N, N-Dimethyl-S-Valine (Dolavaline, Dov)

To a solution of S-valine (5.0 g, 43 mmol) in water (150 ml) was added formaldehyde (37% solution, 15 ml) and 5% palladium on activated carbon (5.0 g). The mixture was hydrogenated (overnight at ambient temperature and pressure), heated at reflux (30 minutes) and the catalyst removed by filtration. The filtrate was concentrated in vacuo. Water and ethanol was added to the residue and solvent evaporated to dryness. The preceding process was repeated (five times) to remove all paraformaldehyde and leave a residue of amorphous powder. Crystallization from ethanol-acetone afforded colorless needles of N,N-dimethyl-S-valine (6.14 g, quantitative): mp 154° C. (reported mp 153° C.) See: Bowmann et al, J. Chem. Soc,. 1950, 1342,: $[\alpha]_D^{30}+40°$(c, 1.0, MeOH), IR (KBr) $v$ 3400, 1602, 1460, 1421, 1395, 1373, 1351, 1331, 1323, 1276, 1191, 1010, 997, 938, 907, 839, 783, 705 cm$^{-1}$, $^1$H NMR (DMSO-d$_6$) $\delta$ 0.848 (d, J=6.5 Hz, 3H, CH$_3$), 0.928 (d, J=6.5 Hz, 3H, CH$_3$), 1.920 (m, 1H, CH), 2.293 (s, 6H, N-CH$_3$), 2.659 (d, J=9.2 Hz, 1H, CH), $^{13}$C NMR $\delta$ 18.97 (CH$_3$), 19.45 (CH$_3$), 26.52 (CH), 73.86 (CH), 170.90 (CO).

EXAMPLE 3

N Z-N-Methyl-(S,S)-Isoleucinol

A solution of Z-(S,S)-isoleucine (10 g, 37.7 mmol) and methyl iodide (18.8 ml, 302 mmol) in tetrahydrofuran (150 ml) was cooled to 0° C. and stirred under argon. Sodium hydride (60% dispersion, 5.42 g, 113 mmol) was carefully added. The suspension was stirred at room temperature for 36 hours. Ethyl acetate (100 ml) was added followed by ice water (300 ml). The aqueous layer was washed with ether (2×200 ml), acidified with concentrated HCl at 0° C. and extracted with ethyl acetate (3×400 ml). The latter extract was washed with water, dried and solvent removed to give N-Me-isoleucine (83% yield See: McDermott et al, Can. J. Cham, 1973, 51, 1915) as a chromatographically homogeneous viscous oil. To a solution of the acid in THF (200 ml, at 0° C. under argon), borane-tetrahydrofuran complex (1M, 60 ml, 60 mmol) was added dropwise and the solution was stirred for 4 hours. Ice (50 g) was added followed by water (200 ml). The product was extracted with ethyl acetate (2×400 ml), washed with water (200 ml), dried, and solvent evaporated to give an oil which was filtered through a column of silica gel. Elution with hexane-acetone (7:3) furnished Z-N-N-methyl(S,S)-isoleucinol as a viscous oil (8.5 g, 85% from Z-isoleucine): $[\alpha]_D^{27}-11.3°$ (c,5.6, CHCl$_3$), IR (NaCl) $v$ 3450, 2963, 2934, 1699, 1454, 1419, 1408, 1342, 1325, 1153, 1114 cm$^{-1}$, $^1$H NMR (CDCl$_3$) $\delta$ 0.84 (d, J=6.7 Hz, 3H, CH$_3$), 0.94 (J=7.6 Hz, 3H, CH$_3$), 1.16-1.81 (m, 3H, CH, CH$_2$), 2.41 (s, 3H, N-CH$_3$), 2.88 (brs, 1H, OH), 2.96 (m, 1H, CH), 3.38 (dd, J=10.2, 9.0 Hz, 2H, CH$_2$O), 4.71 (s, 24, Ar CH$_2$), 7.39 (m, 5H, Ar), and HREIMS (m/z) 265.1675 (2%, M$^+$, calcd. for C$_{15}$H$_{23}$NO$_3$: 265.1678), 234.1498 (6%, M$^+$-CH$_3$O, calcd. for C$_{19}$H$_{20}$NO$_2$: 234.1494), 91.0544 (100%).

EXAMPLE 4

N-Z-N-Methyl-(S, S)-Isoleucinal

Triethylamine (11.03 ml, 79.2 mmol) was added to a solution of Z-N- methyl-(S,S)-isoleucinol (6.0 g, 22.6 mmol) in dimethylsulfoxide (50 ml). The solution was stirred at room temperature for 5 minutes. After cooling to 0° C., sulfur trioxide-pyridine complex (12.6 g, 79.2 mmol) was added (slowly). The reddish solution was stirred at 5° C. for 30 minutes under argon. Ice-water (200 ml) was added and the aldehyde was extracted with ether (2×250 ml). The ethereal solution was successively washed with aqueous citric acid (2×200 ml), water (200 ml), aqueous sodium bicarbonate (2×150 ml), and water (200 ml), dried, and solvent evaporated to give chromatographically pure Z-N-methyl-(S,S)-isoleucinal, 4.66 g, 78%): $[\alpha]_D^{27}-66°$ (c, 4.36, CHCl$_3$), $^1$H NMR (CDCl$_3$) $\delta$ 0.88 (t, J=6.5 Hz, 3 H, CH$_3$), 1.07 (d, J=7.4 Hz, 3 H, CH$_3$), 1.42 (m, 2 H, CH$_2$), 2.06 (m, 1 H, CH), 2.89 (s, 3 H, N-CH$_3$), 4.26 (d, J=9.0 Hz, 1 H, CH), 5.15 (s, 2 H, OCH$_2$), 7.35 (5H, ArH), and 9.69 (s, 1 H, CHO). The aldehyde was used without further purification for the following reaction to avoid racemisation.

EXAMPLE 5

Tert-Butyl (3S, 4S, 5S) - and (3R, 4S, 5S)-3-Hydroxy-4-(N-Z-N-Methyl)-Amino-5-Methyl-Heptanoate To a solution of lithiumdiisopropylamide prepared from n-butyl lithium (13.0 ml, 20 mmol under argon), and diisopropylamine (4.53 ml, 32.4 mmol) in THF (120 ml), at −78° C. with stirring and slow warming (1.5 hrs) up to −20° C. was added (via syringe) tert-butyl acetate (2.7 ml, 20 mmol) to the recooled (−78° C.) solution. The mixture was stirred while warming to −20° over 2 hours. After recooling (−78° C.) isoleucinal prepared according to Example 3 (4.26 g, 16.2 mmol) was added (syringe). Stirring (at −78° C.) was continued 45 minutes and the mixture cautiously treated with ice-water. Additional water (120 ml) was added and the product was extracted with ether (3×150 ml), washed with water, dried and solvent evaporated to give a viscous oil. The crude product was chromatographed (flash silica gel column) and elution with hexane-actone (47:3) gave the 3S-epimer tert-butyl (3S, 4S, 5S)-3-Hydroxy-4-(N-Z,N-Methyl)-Amino-5-Methyl Heptanoate (1.43 g), a mixture (1.93 g) and the 3R-epimer, tert-Buty) (3R,4S,5S)-3-Hydroxy-4-(N-Z,N Methyl)-Amino-5-Methyl-Heptanoate (2.0 g): overall yield 87%. The (3S,4S,5S)-isomer was obtained as a viscous oil: $[\alpha]_D^{35}-37.5°$ (c, 5.0, CHCl$_3$), IR (NaCl) $v$ 2968, 1728, 1698, 1455, 1402, 1369, 1341, 1291, 1154 cm$^{-1}$, $^1$H NMR (CDCl$_3$) $\delta$, two major conformers (1:2 ratio) 0,824, 0.870 (t, J=7.5 Hz, 3H, CH$_3$), 0.980, 1.021 (d, J=6.7 Hz, 3H, CH$_3$), 1.040 (m, 1H, CH$_2$), 1.380 (m, 1H, CH$_2$), 1.45 (s, 9H, C(CH$_3$)$_3$), 2.021, 2.075 (m, 1H, CH), 2.090 (s, 1H, OH), 2.221-2.442 (m, 2H, CH$_2$CO), 2.830, 2.945 (s, 3H, N—CH$_3$), 3.578-3.702 (m, 1H, CH), 4.226-4.337 (m, 1H, CH), 5.122, 5.145 (m, s, 2H, ArCH$_2$O), 7.352 (m, 5H, ArH), and HRFABMS (m/z) 380.2425 [65%, (M+H)$^+$, calcd. for C$_{21}$H$_{34}$NO$_5$: 80.2437].

Anal. Calcd. for C$_{21}$H$_{33}$NO$_5$: C. 66.47, H, 8.76, N, 3.69. Found: C, 66.33, H, 8.78, N, 3.78.

The (3R, 4S, 5S)-isomer was also obtained as a viscous oil: $[\alpha]_D^{35}-3.1°$ (c, 4.25, CHCl$_3$), IR (NaCl) $v$ 2967, 1726, 1700, 1455, 1404, 1368, 1318, 1257, 1154, cm$^{-1}$, $^1$H NMR (CDCl$_3$) $\delta$ two major conformers in a ratio of 1:2, 0.846, 0.880 (t, J-7.5 Hz, 3H, CH$_3$), 0.965, 1.001 (d, J=6.7 Hz, 3 H, CH$_3$), 1.088 (m, 1H, CH$_2$), 1.441, 1.453 (s, 9H, C(CH$_3$)$_3$), 1.500 (m, 1H, CH$_2$), 1.925 (m, 1H, CH), 2.248-2.462 (m, 2H, CH$_2$CO), 2.789, 2.840

(s, 3H, N-CH₃), 3.176–3.389 (1H, OH), 3.807, 3.920 (brm, 1H, CH), 4.252, 4.280 (brm, 1H CH), 5.081–5.172 (m, 2H, ArCH₂O), 7.294–7.356 (m, 5H, ArH), and HREIMS 306.1684 (1%, M⁺ —C₄H₉, calcd. for C₁₇H₂₄NO₄: 306.1706), 234.1492 (10%, M⁺— CHOHCH₂CO₂C₄H₉, calcd. for C₁₄H₂₀NO₂: 234.1498).

Anal. Calcd. for C₂₁H₃₃NO₅: C, 66.47, H, 8.76, N, 3.69. Found: C, 66.45, H, 8.75, N, 3.74.

EXAMPLE 6

Tert-Butyl (3R, 4S, 5S)-3 Methoxy-4-(N-Z-N-Methyl)Amino-5-Methyl-Heptanoate (Z-Dolaisoleuine Tert-Butyl Ester); (Z-Dil-OBuᵗ)

To a cooled (−78° C.) and stirred solution of (3R, 4S, 5S)-heptanoic ester prepared according to Example 5 (1.9 g, 5.0 mmol) which was disposed under argon in dichloromethane (20 ml), boron trifluoride etherate (0.7 ml, 5.69 mmol) was added, and thirty minutes later, an anhydrous solution of dichloromethane (large excess prepared from Diazald) was added. After 1 hour, the polymethylene side-products were removed by filtration, the filtrate was concentrated, the resulting concentrated solution was chromatographed (flash silica gel), and the chromotographic column eluted with hexane-acetone (97:3) to give methyl ether (N-Z-Dil-OBuᵗ) as a pure oil (1.15 g, 67%, based on recovery of starting alcohol): $[\alpha]_D^{35}$ −15.5° (c, 4.85, CHCl₃), IR (NaCl) υ 2968, 1728, 1701, 1455, 1403, 1367, 1314, 1154, 1101 cm⁻¹, ¹H NMR (CDCl₃) δ, two major conformers (ratio of 1:2) 0.847, 0.877 (t, J=7.4 Hz, 3H, CH₃), 0.920, 0.971 (d, J=6.8 Hz, 3H, CH₃), 1.072 (m, 1H, CH₂), 1.250 (m, 1H, CH₂), 1.441, 1.447 (s, 9H, C(CH₃)₃), 1.733 (m, 1H, CH), 2.300–2.469 (m, 2H, CH₂CO), 2.758, 2.786 (s, 3H, N-CH₃), 3.284, 3.389 (s, 3H, OCH₃), 3.827–3.863, 3.877–3.940 (m, 1H, CH), 4.133 (m, 1H, CH), 5.078–5.176 (m, 2H, ArCH₂O), 7.283–7.352 (m, 5H, ArH), and HRFABMS (m/z) 394.2592 [65%, (M+H)⁺, calcd. for C₂₂H₃₆NO₅: 394.2594].

Anal. Calcd. for C₂₂H₃₅NO₅·C₃H₆O: C, 66.49, H, 9.14. Found: C, 66.13, H, 8.94.

EXAMPLE 7

Tert-Butyl (3R, 4S, 5S)-3-Methoxy-4-(N-Methyl)Amino-5-Methyl Heptanoate Hydrochloride (DolaIsoleuine Tert-Butyl Ester Hydrochloride, Dil-OBuᵗ·HCl)

Method A. To Z-dolaisoleuine tert-butyl ester produced according to Example 6 (0.65 g) in ethyl acetate-methanol (3:1, 15 ml) was added 5% Pd/C (0.20 g) catalyst and the mixture was hydrogenated (overnight) at ambient temperature and pressure. Catalyst was removed (filtration) and the filtrate evaporated to dryness. The crude dried filtrate was then dissolved in ether (4 ml), cooled to −60° C., and an ethereal solution of hydrogen chloride (2 ml) was added under anhydrous conditions. The hydrochloride salt precipitated immediately and the excess hydrogen chloride was removed by passing argon into the mixture. The amorphous hydrochloride salt (Dil-OBuᵗ HCl) (0.32 g, 63% yield) was collected by filtration, mp 145°–147° C., $[\alpha]_D^{30}$ 7.25° (c, 4.5, CHCl₃), IR (NaCl) υ 2963, 2930, 2877, 2823, 2765, 1726, 1591, 1482, 1457, 1427, 1393, 1366, 1155, 1091, 1082 cm⁻¹, ¹H NMR (CDCl₃) δ 0.969 (t, J=7.4 Hz, 3 H, CH₃), 1.108 (d, J=9.1 Hz, 3 H, CH₃), 1.440 (s, 9H, C(CH₃)₃), 1.750 (m, 2H, CH₂), 2.025 (m, 1H, CH), 2.656 (dd, J=16.3, 4.1 Hz, 1H, ½ CH₂), 2.756 (dd, J=16.3, 7.6 Hz, 1H, ½ CH₂), 2.80 (brs, 3 H, N-CH₃), 3.074 (brm, 1 H, N-CH), 3.379 (s, 3H, OCH₃), 3.996 (m, 1H, CH—O), and ¹³C NMR (CDCl₃) δ 11.62 (CH₃), 15.78 (CH₃), 26.04 (CH₂), 28.03 (CH₃)₃), 33.92 (CH), 34.63 (NCH₃), 36.97 (CH₂CO), 57.69 (OCH₃), 66.27 (CH), 75.82 (CH), 81.47 (qC), 170.25 (CO).

Anal. Calcd. for C₁₄H₃₀ClNO₃: C, 56.83, H, 10.22. Found: C, 56.58, H, 10.31.

After collecting the hydrochloride salt the filtrate was chromatographed on a column of silica gel and eluted with hexane-acetone (4:1) to yield the corresponding lactam, namely, 4R-methoxy-5S-(1'S-methyl)-propyl-2-pyrrolidinone (90 mg, 29%), as viscous oil, $[\alpha]_D^{30}$ −6° (c, 0.9, CHCl₃), IR (NaCl) υ 1696, 1664, 1620, 1533, 1515, 1502, 1456, 1445, 1368, 1228 cm⁻¹, ¹H NMR (CDCl₃) δ 0.709 (d, J=7 Hz, 3 H, CH₃), 1.000 (t, J=7.6 Hz, 3H, CH₃), 1.323 (m, 1H, ½ CH₂), 1.45 (m, 1H, ½ CH₂), 1.779 (m, 1 H, CH), 2.390 (brd, J=17.8 Hz, 1 H, ½ CH₂), 2.545 (dd, J=17.8, 7.0 Hz, 1H, ½ CH₂), 2.805 (s, 3H, N—CH₃), 3.287 (s, 3H, OCH₃), 3.456 (dd, J=3.4, 1.7 Hz, 1H, CH—N), 3.680 (dt, J=7.0, 1.7 Hz, 1H, CH—O), and HREIMS (m/z) 185.1415 (3%, calcd. for C 185.1416), 128.0711 (100%, M⁺-C₄H₉, calcd. for C₆H₁₀NO₂: 128.0711)

Method B. The formation of the aforesaid pyrrolidinone could be minimized or eliminated by either of the following modifications: (a) by carrying out the hydrogenolysis reaction in a mixture of anhydrous ethyl acetate-methanol (4:1) and promptly removing the catalyst when reaction was complete (two hours) to give >90% yield of the hydrochloride of Example 7 or (b) by using internal hydrogen transfer (cyclohexene), e.g., the methyl ether of Example 6 (50 mg) in anhydrous methanol (10 ml)-cyclohexene (5 ml) is heated at reflux with 10% Pd/C (50 mg) for 5 minutes. The catalyst is then quickly removed by filtration. The evaporation of solvents and addition of ethereal hydrogen chloride provides (35 mg, 93% yield) dolaisoleuine tert-butyl ester hydrochloride.

EXAMPLE 8

N-Boc-S-Prolinol

Triethylamine (7.0 ml) was added to a cooled (0° C.) solution of S-prolinol (4.23 g, 41.9 mmol) in dichloromethane (200 ml), the mixture was stirred for 10 minutes. Thereafter di-tert-butyldicarbonate (11.0 g, 50.3 mmol) was added over 10 minutes. The mixture was stirred at 0° C. for 4 hours and a saturated aqueous solution of citric acid was added. The organic layer was washed with water (2×50 ml), brine (2×50 ml), water (50 ml), and dried. Solvent removal led to N-Boc-Sprolinol as a clear oil. The oil was chromatographed in acetone on a silica gel column. Elution with hexane-ethyl acetate (3:2) afforded N-Boc-S-Prolinol as an amorphous solid (7.63 g, 91%): mp 58°–60° C., $[\alpha]_D^{30}$ −39.5° (c, 15.5, CHCl₃), IR (NaCl) υ 3435, 2975, 2934, 1696, 1672, 1455, 1407, 1367, 1171, 1127, 1107 cm⁻¹, and ¹H NMR (CDCl₃+D₂O) δ 1.46 (s, 9H, C(CH₃)₃), 1.72 (m, 4H, 2×CH₂), 3.36 (m, 2H, CH₂), 3.54 (m, 2H, CH₂), 3.90 (m, 1H, CH—N), HREIMS (m/z) 201 (M⁺, 2%), 170 (30%), 128 (25%), 114 (100%), 70 (98%).

Anal. Calcd. for C₁₀H₁₉NO₃: C, 59.68, H, 9.52, N, 6.99. Found: C, 59.42, H, 9.89, N, 6.94.

The yield (to 99%) of N-Boc-S-prolinol was later increased by reducing the dichloromethane to 100 ml and reaction time at 0° C. to 2.5 hour

EXAMPLE 9

N-Boc-S-Prolinal

Method A. Trifluoroacetic anhydride (4.24 ml, 30 mmol) in dichloromethane (20 ml) was added dropwise (1.5 hrs) to a cooled (−78° C.) solution of dimethylsulfoxide (2.84 ml, 40 mmol) in dichloromethane (20 ml) and stirring was continued at the same temperature for an additional hour. At this point N-Boc-S-prolinol prepared pursuant to Example 8 (4.0 g, 20 mmol) in dichloromethane (15 ml) was added (over 20 min) to the stirred mixture followed 1 hr later by triethylamine (12 ml, 86.1 mmol, over 20 minutes). The resulting solution was allowed to warm to −20° C., stirred for 30 minutes, diluted with brine (20 ml) and extracted with ether (2×250 ml). The ethereal solution was washed with water, dried and concentrated to an oil. A solution of the oil in acetone was quickly filtered through a flash silica gel column. Elution with hexane-acetone (93:7) gave the pure prolinal 8c (2.93 g, 74%) as a colorless oil: $[\alpha]_D^{30} -96°$ (c, 1.19, CHCl$_3$), lit$^3$ $[\alpha]_D^{30} -97°$ (c, 1, CHCl$_3$), and $^1$H NMR (CDCl$_3$)$\delta$ 1.44 (s, 9H, C(CH$_3$)$_3$), 1.96 (m, 4H, 2×CH$_2$), 3.52 (m, 2H, CH$_2$), 4.12 (m, 1 H, CH), 9.49 (brd, 1 H, CHO).

Earlier, this prolinal was obtained from Boc-S-proline methyl ester by DIBAL- reduction but no yields were given. (See: Hanson et al, Tetrahydron Lett., 1986, 27, 3577.)

Method B. After dissolving (room temperature) N-Boc-S-prolinol (2.9 g, 14.4 mmol) in anhydrous dimethylsulfoxide (19 ml), triethylamine (7 ml, 51 mmol) was added. The mixture was stirred at room temperature for 20 min and cooled to 0° C. Sulfur trioxide-pyridine complex (8.0 g, 51 mmol) was added in aliquots over 15 minutes. When addition was complete the mixture was stirred at 0° C. for 2 hours. Ice water (10 ml) was added and the mixture poured into water (30 ml) and extracted with dichloromethane (4×20 ml). The combined extract was washed with water (2×50 ml), saturated aqueous citric acid (2×50 ml), water (2×50 ml), saturated aqueous sodium bicarbonate (2×50 ml), water (2×50 ml), and dried. Solvent was removed and the residue dried under high vacuum to afford (2.26 g, 77%) of the prolinal as a yellow oil which was identical (by TLC in hexane-acetone (4:1) and NMR) with the product of Method A.

EXAMPLE 10

2S-Propionyloxy-1,1,2-Triphenylethanol

To a pyridine (15 ml) solution of 2S-hydroxy-1,1,2-triphenylethanol (4.76 g, 16.4 mmol) prepared See: Ewing et al, Tetrahedron, 1986, 42, 2421; Braun et al, Tetrahedron Lett, 1984, 25, 5031 in 71% yield from S-(+)-methyl mandelate (4.0 g, 24 mmol) was added propionic anhydride (2.56 ml, 20 mmol). The mixture was stirred overnight, precipitated product was collected by filtration, and the filtrate was concentrated by azeotropic (cyclohexane-methanol) distillation of pyridine. Trituration of the concentrate with methanol gave additional propionate ester (total yield 5.47 g, 96%): mp 215°–216° C., $[\alpha]_D^{30} -203.5°$ (c, 1.44, CHCl$_3$), IR (KBr)$\upsilon$ 3525, 3455, 3447, 3439, 1717, 1199, 1182, 1157, 738, 699 cm$^{-1}$, $^1$H NMR (CDCl$_3$)$\delta$1.00 (t, J=7.3 Hz, 3H, CH$_3$), 2.24 (q, J=7.3 Hz, 2 H, CH$_2$), 2.79 (s, 1 H, OH), 6.69 (s, 1 H, CH), 7.02–7.62 (m, 15H, ArH), and EIMS (m/z), 346 (M$^+$, 2%), 256 (5%), 183 (100%), 105 (45%).

Anal. Calcd. for C$_{23}$H$_{22}$O$_3$: C, 79.75, H, 6.40. Found: C, 79.60, H, 6.30.

EXAMPLE 11

N-Boc-2S-3'-[2''-Ethoxy-(1''Hydroxy-1'',1'',2''-Triphenyl) 2'S-Methyl-3'R-Hydroxypropionate]-Pyrrolidine To a solution of lithium diisopropyl amide derived from n-butyl lithium (5.6 ml, 9 mmol) and diisopropylamine (1.4 ml, 10 mmol) in THF (20 ml, at −78° C. under argon) was added a suspension of the propionate prepared in Example 10 (1.38 g, 4 mmol) in THF (15 ml). The reaction mixture was allowed to warm up to room temperature and 2 hrs later the yellow solution was cooled to −95° C. (20 min) (methanol-liquid nitrogen). Next magnesium bromide freshly synthesized from magnesium (0.29 g, 12 mmol) and dibromethane (0.52 ml, 6 mmol in 15 ml of THF), was added followed (1 hour interval) by a solution of Boc-S-prolinal from Example 9 (0.8 g, 4.0 mmol) in THF (10 ml). After 2 hours at −95° C. (methanol-liquid nitrogen), the reaction was terminated with saturated aqueous ammonium chloride (5 ml). The mixture was allowed to warm to 0° C. and ether (400 ml) was added. The ethereal solution was washed with water, dried, and the solvent evaporated to give a glassy solid. An HPLC analysis of the mixture on a reversed phase RP-8 (3m, 100×4.6 mm ID) column (acetonitrile- water, 50→100%, 15 minute gradient and elution at the rate of 1 ml/minute) gave evidence of an isomer ratio of 63:7:15:15. The mixture was preadsorbed on silica gel (10 g) and chromatographed (flash column, 60 mm×200). Elution with hexane-acetone (19:1) afforded unreacted ester (0.22 g), a diasteromeric mixture of (2'R, 3'R), (2'S, 3'S), and (2'R, 3'S) weighing 0.76 g (41.6%) and finally the major product the 2'S, 3'R isomer (0.85 g, 47%). The 2'S, 3'R-isomer was isolated as an amorphous powder from acetone-hexane, mp 128°–130° C., $[\alpha]_D^{30} -146.9°$ (c, 2.45, CHCl$_3$), IR (NaCl)$\upsilon$ 3417, 2977, 1724, 1677, 1450, 1404, 1367, 1166, 754, 697 cm$^{-1}$, $^1$H NMR (DMSO-d$_6$ at 100° C.) $\delta$ 0.836 (d, J=7.1 Hz, 3H, —CH$_3$), 1.426 (s, 9H, (CH$_3$)$_3$), 1.624 (m, 2H), 1.825 (m, 2H), 2.382 (pentet, J=7.1 Hz, 1 H, CH-CO), 3.165 (m, 1 H), 3.377 (m, 1H), 3.685 (dd, J=4.0, $\overline{2.5}$ Hz, 1 H, CH-OH), 4.054 (m, 1 H, —CHN—), 5.467 (s, 1 H, OH), 6.533 (s, 1 H, Ar-CH—O—C=O), 7.063–7.494 (m, 15H, ArH), $^{13}$C NMR (CDCl$_3$)$\delta$ 14.27 (CH$_3$), 23.99 (CH$_2$), 25.69 (CH$_2$), 28.56 (CH$_3$)$_3$), 42.36 (CH), 47.23 (CH$_2$), 59.48 (CH), 72.94 (CH), 79.44 (CH), 79.76 (qC), 80.30 (qC), 126.55 (2×CH), 126.90 (2xCH), 127.32 (3xCH), 127.63 (3xCH), 128.12 (3xCH), 128.59 (2xCH), 142.71 (3xCH), 164.00 (CO), and 173.79 (CO), and EIMS (m/z) 545 (M$^+$, 0.1%), 545 (M$^+$−1, 0.2%), 52.7 (M$^+$—H$_2$O, 4%), 363 (100%), 30.7 (98%), 263 (95%).

Anal. Calcd. for C$_{33}$H$_{39}$NO$_6$: C, 72.64, H, 7.20, N, 2.57. Found: C, 72.21, H, 7.16, N, 2.61.

EXAMPLE 12

N-Boc-2S-3'-[2''-Ethoxy(1''-Hydroxy-1'',1'',2''-Triphenyl) 2'S-Methyl-3'R- Methoxy-Propionate]-Pyrrolidine Method A. Methylation of the 2'S, 3'R-isomer produced according to Example 11 (0.60 g at −78° C.) in dichloromethane (10 ml) with boron triflouride etherate (0.15 ml, under argon) and diazomethane in anhydrous dichloromethane was conducted and the product isolated using the procedures described in Example 6 for obtaining the ether thereof. Elution with hexane-acetone (9:1) gave the methyl ether identified above (0.38 g, 62%) as a powder which crystallized from acetone-hexane as rosettes: mp 130°–132° C., $[\alpha]_D^{30} -168.7°$ (c, 4.15, CHCl$_3$), IR (NaCl)$\upsilon$ 3500, 2977, 1723, 1693, 1449, 1392, 1367, 1166, 1111, 753, 696 cm$^{-1}$, $^1$H NMR (DMSO-d$_6$ at 60° C.) δ 0.794 (d, J=7.0 Hz, 3H, CH$_3$), 1.434 (s, 9H, (CH$_3$)$_3$), 1.640 (m, 1 H, ½ CH$_2$), 1.761 (m, 3H, ½ CH$_2$, CH$_2$), 2.374 (pentet, J=7.0 Hz, 1 H, CH), 3.111 (m, 1 H, ½ CH$_2$), 3.156 (s, 3H, OCH$_3$), 3.400 (m, 1 H, ½ CH$_2$), 3.699 (t, J=7.0 Hz, 1 H, CH—O), 3.900 (m, 1 H, CH—N), 6.582 (s, 1 H, ArCH), 7.056–7.480 (15 H, ArH), and HRFABMS (m/z) 566.3094 [(M+Li)$^+$, calcd. for C$_{34}$H$_{41}$NO$_6$Li: 566.3094]. Anal. Calcd. for C$_{34}$H$_{41}$O$_6$N: C, 72.96, H, 7.38. Found: C, 72.48, H, 7.41. The scale-up of Method A gave erratic results and Method B reported below is preferred.

Method B. As alcohol produced by Example 10 (1.0 g, 1.8 mmol) in dichloromethane (5 ml) was added to a stirred suspension of trimethyloxonium tetrafluoroborate (1.38 g, 9.4 mmol) in dichloromethane (5 ml, under nitrogen) at room temperature. Proton sponge (2.0 g, 9.4 mmol) was added and the mixture stirred at room temperature for 16 hours. The solvent was removed and the resulting yellow solid was preadsorbed on silica gel and subjected to flash column chromatography. Elution with 9:1 hexane-acetone afforded the pure methyl ether identified above (0.51 g, 50%). The specimens of this methyl ether prepared by Methods A and B were identical (by TLC hexane-acetone, 7:3 and NMR).

EXAMPLE 13

N-Boc 2S-3'-[2"Ethoxy(1"-Hydroxy-1",1",2"-Triphenyl) 2'R-Methyl-3'R-Methoxy-Propionate]-Pyrrolidine A solution of potassium tert-butoxide (1.0M solution in THF, 0.65 ml, 0.65 mmol, 2.2 eqv.) was added to the (2'S, 3'R)-ester from Example 12 (0.165 g, 0.3 mmol) in THF (2 ml at −20° C. under nitrogen) and the stirred solution turned bright yellow. After warming to −15° C. the epimerization was stopped with saturated aqueous citric acid, diluted with the same solution and extracted with dichloromethane (3×10 ml). The combined extract was washed with water and dried. Solvent removal gave a clear yellow oil (0.16 g). Flash chromatography on silica gel (19:1 hexane-acetone, eluant) afforded as a clear oil the 2'R, 3'R-epimer of the above identified pyrrolidine (90 mg, 57%). Recrystallization from acetone-hexane gave fine crystals: mp 130°–132° C., $[\alpha]_D^{30} -154.6°$ (c, 0.01, CHCl$_3$), IR (NaCl)$\upsilon$ 3420, 2977, 1733, 1674, 1408, 1367, 1244, 1166, 757, 698 cm$^{-1}$, $^1$H NMR (CDCl$_3$) δ 1.150 (d, J=7.0 Hz, 3H, CH$_3$), 1.521 (s, 9H, (CH$_3$)$_3$), 1.650 (m, 2H, CH$_2$), 1.913 (m, 1H, ½ CH$_2$), 2.200 (m, 1 H, ½ CH$_2$), 2.641 (distorted dq, J=7.0, 1.1 Hz, 1 H, CH), 3.020 (m, 1 H, ½ CH$_2$), 3.180 (m, 1 H, ½ CH$_2$), 3.373 (s, 3 H, OCH$_3$), 3.689 (m, 1 H, CH—N), 4.172 (dd, J=10.4, 1.1 Hz, 1 H, CH—O), 5.687 (s, 1 H, OH), 6.845 (s, 1 H, ArCH—O), 6.995–7.689 (m, 15 H, ArH), and HRFABMS (m/z) 566.3101 [(M+Li)$^+$, calcd. for C$_{34}$H$_{41}$NO$_6$Li: 566.3094].

Anal. Calcd. for C$_{34}$H$_{41}$NO$_6$: C, 72.96, H, 7.38, N, 2.50. Found: C, 72.73, H, 7.68, N, 2.47.

EXAMPLE 14

N-Boc-2S-3'-(2'S-Methyl-3'R-Methoxy-Propionic Acid)-Pyrrolidine; [Boc (2S, 2'S, 3'R)Dolaproine]; [Boc-(2S, 2'S, 3'R)-Dap]

Hydrogen was passed through a mixture of benzyl ester from Example 12 (0.41 g) in ethyl acetate-methanol (3:1, 50 ml) and 10% Pd/C (0.15 g) at ambient temperature and pressure for 48 hours. The catalyst was collected on celite and washed thoroughly with ethyl acetate. The filtrate was evaporated to an oil which was chromatographed on a column of silica gel. Elution with a gradient of 7:3 hexane-acetone to acetone led to Boc-(2S, 2'S,3'R)-Dap (0.17 g, 80.7%,). Recrystallization from acetone-hexane afforded a pure specimen as rods: mp 105°–108° C., $[\alpha]_D^+ -107.5°$ (c, 0.4, CHCl$_3$), IR (NaCl)$\upsilon$ 2934, 1695, 1654, 1417, 1400 cm$^{-1}$, $^1$H NMR (DMSO-d$_6$ at 120° C.) δ 1.000 (d, J=7.2 Hz, 3H, CH$_3$), 1.400 (s, 9 H, (CH$_3$)$_3$), 1.700 (m, 1 H, ½ CH$_2$), 1.810 (m, 1 H, ½ CH$_2$), 1.910 (m, 2 H, CH$_2$), 2.360 (dq, J=9.2, 7.2 Hz, 1 H, CH), 3.180 (m, 1 H, ½ CH$_2$), 3.315 (s, 3 H, OCH$_3$), 3.449 (m, 1 H, ½ CH$_2$), 3.846 (m, 1 H, CH—N), 3.885 (dd, J=9.2, 2.2 Hz, 1 H, CH—O), and HRFABMS (m/z) 294.1900 [(M+Li)$^+$, calcd. for C$_{14}$H$_{25}$NO$_5$Li: 294.1893].

Anal. Calcd. for C$_{14}$H$_{25}$NO$_5$: C, 58.52, H, 8.79, N, 4.87. Found: C, 58.53, H, 8.91, N, 4.81.

EXAMPLE 15

N-Boc-2S-3'-(2'R-Methyl-3'R-Methoxy-Propionic Acid)-Pyrrolidine; [Boc-(2S, 2'R, 3'R-Dolaproine]; [Boc-(2S, 2'R, 3'R)-Dap]

To a mixture of methanol (3 ml) and 10% Pd/C (0.30 g, under nitrogen at room temperature) was added with stirring a solution of (1'R, 2'R) benzyl ester prepared according to Example 13 (0.302 g) in methanol (2 ml). The system was evacuated and flushed with hydrogen gas from a rubber balloon attachment for 12 hours. The product was passed through a short silica gel column in acetone to remove the catalyst (washed well with methanol). Solvent was removed and the resulting glassy solid was dissolved in acetone. The solution was filtered through a short bed of silica gel. Solvent removal led to N-Boc-(2S, 2'R, 3'R)-Dap as a solid (0.15 g, 94%) which recrystallized from acetone-hexane as shiny needles: mp 138°–142° C., $[\alpha]_D^{30} -40°$ (c, 3.0, CH$_3$OH), IR (NaCl)$\upsilon$ 2976, 1696, 1685, 1675, 1669, 1663, 1653, 1640, 1594, 1457, 1423 cm$^{-1}$, $^1$H NMR (DMSO-d$_6$ at 100° C.) δ 1.111 (d, J=6.3 Hz, 3 H, CH$_3$), 1.447 (s, 9 H, (CH$_3$)$_3$), 1.662 (m, 1 H), 1.850 (m, 2 H), 1.943 (m, 1 H), 2.174 (brm, 1 H, H-2'), 3.154 (m, 1 H, H-5), 3.426 (m, 1 H, H-5), 3.833 (brm, 1 H), 3.915 (brm, 1 H), and HRFABMS (m/z) 294.1901 [(M+Li)$^+$, calcd. for C$_{14}$H$_{25}$NO$_5$Li: 294.1893].

EXAMPLE 16

N-Boc-2S-3'-[Methyl2'S-Methyl-3'R-Hydroxy-Propionate]Pyrrolidine

A mixture of hydroxy benzyl ester prepared pursuant to Example 11 (500 mg, 0.92 mmol) in ethyl acetate-methanol (1:1, 115 ml) and 5% Pd/C (500 mg) was hydrogenated at ambient temperature and pressure for 36 hours. Catalyst was removed via filtration through celite and thoroughly washed with ethyl acetate. Solvent was removed under reduced pressure and resulting residue was dissolved in ether and esterified by addition of excess diazomethane. Ether was removed in vacuo and the residual gum was preadsorbed on silica gel (5 g) in acetone and then chromatographed over a silica gel column. Elution of the column with hexane-acetone (97:3) gave chromatoraphically homogeneous ester N-Boc-2S-3'-[Methyl2'S-Methyl-3'R-Hydroxy-Propionate]-Pyrrolidine as a viscous oil (180 mg, 68.4%),

[α]$_D^{30}$ −63.8° (c, 2.35, CHCl$_3$), IR (NaCl)υ 3450, 2975, 2953, 1741, 1694, 1394, 1367, 1194, 1167, 1119, 1107 cm$^{-1}$, $^1$H NMR (CDCl$_3$)δ 1.230–1.266 (m, 3 H, —CH$_3$, signal became doublet at 65° in DMSO-d$_6$, J=7.0 Hz), 1.463 (s, 9 H, (CH$_3$)$_3$), 1.747 (m, 1 H, ½CH$_2$), 1.829 (m, 1 H, ½CH$_2$), 1.905 (m, 2 H, CH$_2$), 2.545 (pentet, J=7.0 Hz, 1 H, CH—CO$_2$), 3.269 (m, 2 H, CH$_2$), 3.708 (s, 3 H, OCH$_3$), 3.950–4.100 (m, 2 H, CH—O, CH—N), $^{13}$C NMR (all the signals were either very broad or split into two because of stable conformers) δ 14.68 (CH$_3$), 24.27 (CH$_2$), 25.37 (CH$_2$), 28.49 ((CH$_3$)$_3$), 42.32, 42.84 (CH), 47.21, 47.54 (CH$_2$), 51.75 (OCH$_3$), 59.50, 59.85 (CH$_2$), 73.95 (CH), 79.65 (C°), 156.0 (CO), 176.14 (CO), HRFABMS (m/Z) 294.1886 [(M+Li)+, calcd. for C$_{14}$H$_{25}$NO$_5$Li: 294.1893].

Anal. Calcd. for C$_{14}$H$_{25}$NO$_5$: C, 58.50, H, 8.77, N, 4.87. Found: C. 58.31, H, 8.85, N, 4.77.

EXAMPLE 17

(4R)-Hydroxy-(3S)-Methyl-(5S)-Pyrrolizidin-2-One

To a solution of the Boc-methyl ester prepared by Example 16 (137 mg, 0.48 mmol) in dichloromethane (5 ml) was added trifluoroacetic acid (1.5 ml) at 0° C. The solution was stirred for one hour under nitrogen. Solvent was evaporated under a stream of nitrogen and water (3 ml) was added followed by potassium carbonate (200 mg). The mixture was heated on a steam bath for 15 min and then allowed to cool to room temperature. The aqueous solution was extracted with ethyl acetate (3×20 ml). Combined ethyl acetate extract was washed with water (20 ml), dried (Na$_2$SO$_4$) and evaporated to give an oily material. Chromatography on a flash column and elution with hexane-acetone (3:1) afforded the minor base racemized product (3R, 4R) pyrrolizidinone (8.3 mg, 12%), fine needles from acetone-hexane mp 100°–101° C., [α]$_D^{25}$ +2.0° (c, 3.7, CH$_3$OH), IR (NaCl)δ 3335, 2976, 2949, 2880, 1681, 1659, 1457, 1447, 1367, 1107 cm$^{-1}$, $^1$H NMR (CDCl$_3$) δ 1.213 (d, J=7.0 Hz, 3 H, —CH$_3$), 1.488 (m, 1 H, ½ CH$_2$), 2.000 (m, 2 H, —CH$_2$), 2.170 (m, 1 H, ½CH$_2$), 2.725 (pentet, J=7.0 Hz, 1 H, —CH— CO), 3.572 (m, 1 H, —CH$_2$), 3.667 (m, 2 H, —CH—O, CH—N), $^{13}$C NMR (CDCl$_3$)δ 12.66 (CH$_3$), 26.64 (CH$_2$), 29.95 (CH$_2$), 41.72 (CH$_2$), 49.00 (CH), 66.44 (CH), 82.15 (CH), 173.97 (CO), and HREIMS (m/z) 155.0943 (M+, 217, calcd. for C$_8$H$_{13}$NO$_2$: 155.0947), continued elution of the column provided the major product, namely, (4R)-Hydroxy-(3S)- methyl-(5S)-Pyrrolizidin-2-One (40 mg, 58.6%), prisms from acetone- cyclohexane, mp 121°–122° C., [α]$_D^{30}$−115.1° (c, 1.85, CHCl$_3$), IR (NaCl)υ 3251, 2985, 2979, 2934, 1677, 1444, 1312 and 1089 cm$^{-1}$, $^1$H NMR (CDCl$_3$) δ 1.267 (d, J=7.6 Hz, 3 H, —CH$_3$), 1.482 (ddd, J=17.5, 12.6, 8.6 Hz, 1 H, ½CH$_2$), 2.305 (m, 2 H, CH$_2$), 2.170 (dddd, J=17.5, 12.6, 8.4, 3.6 Hz, 1 H, 1/1CH$_2$), 2.720 (pentet, J=7.6 Hz, 1 H, —CHCO), 3.043 (ddd, J=12, 8.4, 4.7 Hz, 1 H, ½CH$_2$), 3.571(dt, J=11.6, 7.7 Hz, 1H, ½CH$_2$), 3.744 (ddd, J=12.4, 8.7, 6.3 Hz, 1H, CH—N), 4.195 (dd, J=12.0, 6.0, Hz, 1H, CH—O), $^{13}$C NMR (CDCl$_3$) δ 10.26 (CH$_3$), 26.75 (CH$_2$), 29.75 (CH$_2$), 41.51 (CH$_2$), 47.04 (CH), 66.83 (CH), 74.81 (CH), 176.72 (CO), HREIMS (m/z) 155.0952 (M+, 31%, calcd. for C$_8$H$_{13}$NO$_2$: 155.0947).

Anal. Calcd. for C$_8$H$_{13}$NO$_2$: C, 61.9, H, 8.44, N, 9.03. Found: C, 61.57, H, 8.63, N, 8.77.

EXAMPLE 18

N-Boc-S-Phenylalaninol

Method A. Triethylamine (4.3 ml, 30 mmol) was added to a cooled (−10° C.) solution (under argon) of S-phenylalaninol (3.9 g, 25.8 mmol) in dichloromethane (120 ml) followed by di-tert-butyl dicarbonate (6.6 g, 30 mmol) in dichloromethane (10 ml). The solution was stirred for 1.5 hours, washed with saturated aqueous citric acid (2×20 ml), water (50 ml), dried and solvent evaporated to yield a colorless solid N-Boc-S-Phenylalaninol which crystallized from ethyl acetate-hexane as fine needles (6.1 g, 94%): mp 89°–91° C., [α]$_D^{30}$−28.0° (c, 2.7, CHCl$_3$), IR (NaCl)υ 3359, 2980, 2931, 1687, 1528, 1497, 1367, 1251, 1171, and 700 cm$^{-1}$, $^1$H NMR (CDCl$_3$)δ, 1.409 (s, 9 H, (CH$_3$)$_3$), 2.830 (d, J=5.2 Hz, 2 H, CH$_2$), 3.546 (dd, J=11.2, 5.2 Hz, 1H, ½ CH$_2$O), 3.660 (dd, J=11.2, 3.6 Hz, 1H, ½ CH$_2$O), 4.735 (brd, J=7.2 Hz, 1H, NH), 7.198–7.315 (5 H, ArH), EIMS (m/z) 251 (M+, 0.17), 160 (354).

Anal. Calcd. for C$_{14}$H$_{21}$NO$_3$: C, 66.91, H, 8.42, N, 5.57. Found: C, 66.45, H, 8.67, N, 5.59.

Method B. A 1M solution of diborane in THF (200 ml, 200 mmol) was slowly added (under argon) to a cool (0° C.) solution of Boc-S-Phe (26.3 g, 99 mmol) in THF (50 ml). When addition was complete stirring was continued 1.5 hr. The mixture was poured into water (200 ml), extracted with ether (3×300 ml) and the ethereal extract was washed with water and dried. Removal of solvent yielded N-Boc-S-Phenylalaninol as a solid weighing 22.8 g (92%), identical (by TLC (hexane-ethyl acetate 1:1), NMR) with the Phenylalaninol produced by Method A.

EXAMPLE 19

N-Boc-S-Phenylalaninal

A solution of Boc-phenylalaninol produced pursuant to Example 18 (5.3 g, 21.1 mmol) in anhydrous dimethylsulfoxide-triethylamine (40 ml) was oxidized with sulfur trioxide-pyridine complex (10.0 g, 63.3 mmol) and the aldehyde N-Boc-S-Phenylalaninal was isolated essentially as summarized for obtaining the aldehyde of Example 9 (Method B). In this case the product precipitated upon addition of water to the reaction mixture. The oily aldehyde was dried under high vacuum to N-Boc-S phenylalaninal as a powder (5.0 g, 95%): mp 67°–69° C., [α]$_D^{30}$ −37.5° (c, 1.0, CHCl$_3$), IR (NaCl)υ 3417, 3415, 1733, 1690, 1521, 1506, 1498, 1169 cm$^{-1}$, and 1H NMR (CDCl$_3$) δ 1.43 (s, 9 H, (CH$_3$)$_3$), 3.10 (d, J=6.9 Hz, 2H), 4.40 (m, 1 H, —CH), 5.00 (brs, 2 H, ArCH$_2$), 7.10–7.30 (m, 6 H, ArH—NH), 9.62 (s, 1 H, CHO), EIMS (m/z) 249 (M+, 2%), 220 (12%), 164 (15%), 120 (40%).

In order to prevent racemisation the aldehyde was not further purified but instead was employed directly in Example 20, infra.

EXAMPLE 20

2-(N-Boc-1′S-Amino-2′-Phenyl-ethyl)-2(R,S)-Thiazolidine [N-Boc-2(3),4(5)-Tetrahydro-Dolaphenine], [N-Boc-2(3), 4(5)-4H-Doe]

A solution of Boc-S-phenylalaninal prepared according to Example 19 (4.3 g, 17.3 mmol) and 2-aminoethanethiol (1.6 ml, 20.7 mmol) in anhydrous (sodium) benzene (50 ml) was stirred at room temperature under argon for 4 hours. The solvents were evaporated and excess reagent was removed by quick filtration through a pad of silica gel (vacuum column, hexane-ethyl acetate, 7:3). Crystallization of the residue from acetone-hexane furnished the diastereomeric mixture corresponding to 2(2), 4(5)-4H-tetrahydro-Doe as crystals (5.21 g, 98%): mp 73°–74° C., $[\alpha]_D^{30}$ 0.0° (MeOH), IR (NaCl)υ 3309, 3304, 2975, 1709, 1496, 1454, 1366, 1247, and 1168 cm$^{-1}$, $^1$H NMR (CDCl$_3$)δ, a diastereomeric ratio of 2:1, 1.380, 1.400 (s, 9 H, (CH$_3$)$_3$), 2.675 (m, 2 H), 2.81 (M, 2 H), 2.95 (m, 2 H), 3.58 (dd, J=5.0 Hz, 1H, CH), 4.388 (m, 1H, CH), 4.514 (brs, 1 H, NH), 4.98 (d, J=9.6 Hz, 1 H, NH), 7.20–7.31 (5 H, ArH), and HRFABMS (m/z) 315.1717 [(M+Li)$^+$, calcd. for C$_{16}$H$_{24}$N$_2$O$_2$SLi: 315.1719].

Anal. Calcd. for C$_{16}$H$_{24}$N$_2$O$_2$S: C, 62.31, H, 7.84, N, 9.08. Found: C, 62.62, H, 7.90, N, 9.13.

EXAMPLE 21

2(1'S-Boc-Amino-2'-Phenyl-ethyl)-Thiazole (N-Boc-S-Dolaphenine, Boc-S-Doe)

Method A. To a suspension of battery grade (Type M) manganese dioxide (14 g) in anhydrous benzene (80 ml) was added the thiazolidine prepared according to Example 20 (2.0 g) in benzene (50 ml). The mixture was stirred under argon at 55° C. for 24 hours, additional manganese dioxide (7 g) was added and stirring continued another 48 hours. The solution was filtered through a narrow bed of silica gel and eluted with benzene (200 ml), ethyl acetate (1000 ml), chloroform (200 ml), and chloroform-acetone (1:1, 200 ml). The combined eluant was evaporated to dryness and the residue was further flash chromatographed (200×30 mm silica gel column, hexane-ethyl acetate, 19:1) to yield the thiazole, Boc-S-Doe (0.25 g, 13%) as an amorphous solid which crystallized from ethyl acetate-hexane as granules, mp 106°–107° C., $[\alpha]_D^{30}$−23.3° (c, 0.6, CHCl$_3$), IR (NaCl)υ 3290, 2977, 1700, 1517, 1498, 1454, 1440, 1392, 1367, 1249, 1168, 698 cm$^{-1}$, $^1$H NMR (CDCl$_3$) δ 1.400, (s, 9 H, (CH$_3$)$_3$), 3.285 (d, J=6.4 Hz, 2 H, ArCH$_2$), 5.276 (m, 2 H, NH,CH), 7.076 (m, 2 H, ArH), 7.185–7.246 (m, 3 H, ArH), 7.251 (d, J=3.2 Hz, 1 H, H-2), 7.747 (d, J=3.2 Hz, 1 H, H-3), and HRFABMS (m/z) 311.1411 [(M+Li)$^+$, calcd. for C$_{16}$H$_{20}$N$_2$O$_2$SLi. 311.1406].

Anal. Calcd. for C$_{16}$H$_{20}$N$_2$O$_2$S: C, 63.13, H, 6.63, N, 9.20. Found C, 63.14, H, 6.62, N, 9.23.

Continued elution of the flash column afforded a dihydrothiazole (53 mg, 3%): mp 98°–100° C., IR (NaCl) 3400, 2977, 1714, 1583, 1482, 1449, 1367, 1337, 1244, 1160, 772 cm$^{-1}$, $^1$H NMR (CDCl$_3$) 1.343 (s, 9 H, (CH$_3$), 3.383 (t, J=8 Hz, 2 H, H-5), 4.372 (t, J=8 Hz, 2 H, H-4), 6.650 (br, 1 H, NH), 6.707 (s, 1 H, olefinic CH), 7.23–7.504 (m, 5 H, ArH), and HRFABMS (m/z) 311.1396 [(M+Li)$^+$, calcd. for C$_{16}$H$_{20}$N$_2$O$_2$SLi: 311.1406]

Anal. Calcd. for C$_{16}$H$_{20}$N$_2$O$_2$S: C, 63.13, H, 6.62, N, 9.20. Found: C, 63.09, H, 6.67, N, 9.07.

Method B. The thiazole Boc-S-Doe was routinely prepared by the following procedure. The activated (cf. Method A) manganese dioxide (6.0 g) was mixed with dry dioxane and the resulting slurry was added to a dry glass column (7.5 mm I.D.). The column was lightly packed by eluting with dioxane under a positive pressure of nitrogen. The thiazolidine 2-(N-Boc-1'S-Amino-2'-Phenyl-ethyl)-2(R,S)-Thiazolidine prepared according to Example 20 (0.20 g) in dry dioxane (4 ml) was allowed to flow through the column over a 4 hour contact time. After removing an initial fraction containing side-products the next fraction provided Boc-Doe in average yields of 14%.

Dehydrogenation of the thiazolidine of Example 20 to Boc-S-Doe was very sensitive to quality of the manganese dioxide. The battery grade manganese dioxide identified above gave the most consistent results (to 18% yields). When poorer quality manganese dioxide was used, the yields dropped from very low to none. For example, freshly prepared manganese dioxide gave maximum yields of Boc-S-Doe in the 10% range while the Aldrich Chemical Co. product resulted in some 5% yields.

EXAMPLE 22

S-Dov-S-Val-OBu$^t$

To a solution of dolavaline (0.88 g, 6.06 mmol) in DMF (10 ml) was added S-Val-OBu$^t$ hydrochloride (1.27 g, 6.06 mmol) followed by THF (100 ml). After warming (for dissolution), hydroxybenzotriazole (2.08 g, 15.15 mmol) and N-methylmorpholine (0.67 ml, 6.06 mmol) were added. Upon cooling to 0° C. over 2 hours dicyclohexylcarbodiimide (1.5 g, 7.28 mmol) was added and the mixture stirred at room temperature overnight. The precipitate was collected, the filtrate was successively concentrated in vacuo, triturated with acetone, refiltered, concentrated and poured into ether (200 ml). The ethereal solution was washed with saturated aqueous sodium bicarbonate (2×50 ml), cold water (2×50 ml), dried, solvent evaporated, and the residue chromatographed (flash column). Elution with hexane-acetone (85:15) furnished S-Dov-S-Val-OBu$^t$ (1.45 g, 80%) as a colorless powder. Recrystallization from acetone-hexane gave flakes: mp 96°–97° C., $[\alpha]_D^{30}$−17.2° (c, 3.6, CHCl$_3$), IR (NaCl)υ 3315, 3276, 2965, 1729, 1643, 1542, 1466, 1367, 1312, 1234, 1228, 1172, 1148 cm$^{-1}$, and $^1$H NMR (CDCl$_3$) δ 0.910 (d, J=6.90 Hz, 3H —CH$_3$), 0.932 (d, J=6.7 Hz, 3 H, CH$_3$), 0.965 (d, J=6.8 Hz, 3 H, —CH$_3$), 0.996 (d, J=6.9 Hz, 3 H, —CH$_3$), 1.456 (s, 9 H, (CH$_3$)$_3$), 2.096 (heptet, J=6.7 Hz, 1 H, —CH), 2.136 (heptet, J=6.9 Hz, 1 H, —CH), 2.280 (s, 6 H, N—(CH$_3$)$_2$), 2.462 (d, J=5.8 Hz, 1 H, Dov—CH), 4.424 (dd, J=8.8, 7.0 Hz, 1 H, Val—CH), 6.821 (d, J=8.3 Hz, 1 H, NH), $^{13}$C NMR (CDCl$_3$) 17.43 (CH$_3$), 17.78 (CH$_3$), 19.33 (CH$_3$), 20.22 (CH$_3$), 27.64 (CH), 28.05 ((CH$_3$)$_3$), 31.22 (CH), 43.24 (N—CH$_3$), 57.22 (N—CH), 76.54 (N—CH), 81.72 (C—O), 171.20 (CO), 171.56 (CO), and HREIMS (m/z) 300.2407 (M$^+$, calcd. for C$_{16}$H$_{32}$N$_2$O$_3$:300.2413.

Anal. Calcd. for C$_{16}$H$_{32}$N$_2$O$_3$: C, 63.97, H, 10.73, N, 9.32. Found: C, 64.46, H, 11.22, N, 9.42

EXAMPLE 23

S-Dov-S-Val

A solution of the dipeptide ester S-Dov-S-OBu$^t$ prepared according to Example 22 (0.67 g) in dichloromethane (3 ml) trifluoroacetic acid (3 ml) at 0° C. was stirred at room temperature for an hour. The solvent was evaporated, ethanol was added and evaporated. The residue was crystallized from ether-hexane to provide the S-Dov-S-Val dipeptide as rosettes (0.54 g, 98%): mp 180°–182° C., $[\alpha]_D^{30}$+5.1° (c, 2.55, CHCl$_3$), IR, (NaCl)υ 3339, 3058, 2939, 1722, 1670, 1545, 1467, 1449, 1420, 1400, 1374, 1202, 1140 cm$^{-1}$, $^1$H NMR (CDCl$_3$) δ 0.858 (d, J=6.6 Hz, 3 H, —CH$_3$), 0.963 (d, J=6.9 Hz, 3 H, CH$_3$), 0.971 (d, J=6.9 Hz, 3 H, CH$_3$), 1.058 (d, J=6.6 Hz, 3 H, CH$_3$), 2.200 (m, 1 H, —CH), 2.330 (m, 1 H, —CH), 2.895 (s, 3 H, N—CH$_3$), 3.030 (s, 3 H, N—CH₃), 4.573 (d, J=10.8 Hz, 1 H, Dov—CH), 4.687 (dd, J=7.2, 3.6 Hz, 1 H, Val- —CH), 8.366 (d, J=7.2 Hz, 1 H, NH), 10.607 (brs, 1 H, CO₂H), (CDCl₃)δ 17.86 (CH₃), 18.24 (CH₃), 18.96 (CH₃), 19.39 (CH₃), 27.70 (CH), 31.99 (CH), 36.71 (N—CH₃), 43.16 (N—CH₃), 57.42 (CH), 70.30 (CH), 166.77 (CO₂H), 174.33 (CO), and HREIMS (m/z) 244.1777 (M+, calcd. for C₁₂H₂₄N₂O₃: 244.1787).

Anal. Calcd. for C₁₂H₂₄N₂O₃. TFA: C, 46.92, H, 7.03, N, 7.81. Found: C, 46.83, H, 7.25, N, 7.70.

EXAMPLE 24

N-Z-(S)-Val-(3R, 4S, 5S)-Dil-OBuᵗ

To a solution of N-Z-S-valine (84 mg, 0.34 mmol) in anhydrous chloroform (8 ml) cooled to −23° C. was added, with stirring (under argon), N-methylmorpholine (0.074 ml, 0.68 mmol) and 10 minutes later pivaloyl chloride (0.042 ml, 0.34 mmol). The mixture was stirred at −23° C. for 3 hours and solid (3R, 4S, 5S)-Dil-OBuᵗ HCl (50 mg, 0.17 mmol) and N-methylmorpholine (0.02 ml, 0.18 mmol) were added. The mixture was stirred at −23° for 2 hours and then concentrated to 2 ml by sweeping with argon at room temperature and stirring was continued for three days. Chloroform (20 ml) was added and the solution was washed with saturated aqueous citric acid (2×10 ml), water (10 ml), aqueous sodium bicarbonate (2×10 ml), and water (10 ml), dried and solvent evaporated. Flash chromatography (silica gel column) using hexane-acetone (19:1) as eluent yielded the dipeptide N-Z-S-Val-(3R,4S, 5S)-Dil-OBuᵗ (65 mg, 80%) as a viscous oil: [α]$_D^{30}$ −58° (c, 0.5, CHCl₃), IR (NaCl)υ 3300, 2934, 1726, 1640, 1522, 1507, 1499, 1369, 1154 cm⁻¹, ¹H NMR (CDCl₃)δ 0.831 (t, J=7.4 Hz, 3 H, CH₃), 0.910 (d, J=6.7 Hz, 3 H, CH₃), 0.953 (d, 6.6 Hz, 3 H, CH₃), 1.003 (d, J=6.7 Hz, 3 H, (CH₃), 1.256 (m, 1 H, ½ CH₂)m 1.385 (m, 1 H, ½ CH₂), 1.452 (s, 9 H, C(CH₃)₃), 1.663 (m, 1 H, CH), 1.995 (heptet, J=6.5 Hz, 1 H, CH), 2.299 (dd, J=15.5, 9.2 Hz, 1 H. ½ CH₂CO), 2.403 (dd, J=15.5, 2.0 Hz, 1 H, ½ CH₂CO), 2.953 (s, 3 H, N—CH₃), 3.336 (s, 3 H, OCH₃), 3.878 (brm, 1 H, —CH—O), 4.509 (dd, J=9.2, 5.6 Hz, 1 H, Val- —CH), 4.721 (brm, 1 H, Dil—CH—N), 5.092 (s, 2 H, ArCH₂O), 5.516 (d, J=9.2 Hz, 1 H, Val-NH), 7.347 (m, 5 H, ArH), ¹³C NMR (CDCl₃) δ 10.95 (CH₃), 15.84 (CH₃), 17.04 (CH₃), 20.08 (CH₃), 25.85 (CH₂), 28.08 (CH₃)₃, 31.12 (CH), 33.30 (N—CH₃), 38.50 (CH₂CO), 56.04 (CH), 57.87 (OCH₃), 66.76 (ArCH₂O), 78.16 (CH), 80.86 (qC), 127.85 (2×CH), 128.02 (CH), 128.48 (2×CH), 136.53 (qC), 156.52 (CO), 171.08 (CO), 171.08 (CO), 173.17 (CO), and HRFABMS (m/z) 493.3278 [(M+H)+, 30%, calcd. for C₂₇H₄₅N₂O₆: 493.3278].

EXAMPLE 25

S-Dov-S-Val-(3R, 4S, 5S)-Dil-OBuᵗ

A solution of dolavaline (0.73 g, 5 mmol) in pyridine (2 ml) was cooled to 0° C. and pentafluorophenol trifluoroacetate [2.1 g, (prepared in 96% yield by heating pentafluorophenol (3.68 g, 20 mmol) and trifluoroacetic anhydride (4.24 ml, 30 mmol) in refluxing benzene (7 ml))] was added under argon. The solution was stirred at room temperature for 30 minutes, ethyl acetate (50 ml) was added and the organic phase was washed with 10% aqueous sodium bicarbonate (2×20 ml), water (20 ml), dried and solvent evaporated to an oil. The oily active ester was purified by chromatography on a column of silica gel and eluted with hexane-acetone (99:1) to give dolavaline pentafluorophenol ester (1.2 g, 77%) (Dov-Pfp).

To a solution of Z-(S)-Val-(3R,4S,5S)-Dil-OBuᵗ (83 mg, 0.17 mmol) and Dov-Pfp (0.14 g, 0.45 mmol) in anhydrous dioxane (8 ml), was added 10% Pd/C (0.10 g) catalyst. The mixture was saturated with hydrogen overnight under anhydrous conditions and at ambient temperature and pressure. The catalyst was removed by filtration and solvent evaporated. The residue was dissolved in benzene (5 ml), and treated with trifluoroacetic anhydride (0.5 ml) at 0° C. under argon. The solution was stirred for 10 minutes (to form pentafluorophenol trifluoroacetate), solvent was removed, the residue was chromatographed on a column of SEPADEX$^R$LH-20 in 3:2 dichloromethane-methanol and final isolation was realized by flash chromatography (silica gel column, eluant, hexane-acetone, 4:1), to give the tripeptide S-Dov-S-Val-(3R, 4S,5S)-Dil-OBuᵗ as a powder (70 mg, 83%), which crystallized from acetone-hexane as rosettes: mp 104°-106° C., [α]$_D^{28}$ −50° (c, 1.06, MeOH), IR (NaCl)υ 3300, 2692, 1734, 1664, 1623, 1521, 1472, 1465, 1457, 1369, 1154 cm⁻¹,¹H NMR (CDCl₃)δ 0.806(t,J=7.5 Hz, 3H, CH₃), 0.921 (d, J =6.7 Hz, 3 H, CH₃, 0.949 (d, J=6.4 Hz, 3 H, CH₃), 0.964 (d, J=5.6 Hz, 3 H, CH₃), 1.000 (d, J=6.8 Hz, 3 H, CH₃), 1.025 (d, J=6.8 Hz, 3 H, CH₃), 1.257-1.381 (m, 2 H, CH₂), 1.458 (s, 9 H, C(CH₃)₃), 1.677 (m, 1 H, CH), 2.036 (heptet, J=6.6 Hz, 1 H, CH), 2.071 (heptet, J=6.6 Hz, 1 H, CH), 2.252 (s, 6 H, N—(CH₃)₂), 2.296 (d, J=6.2 Hz, 1 H, CH), 2.309 (m, 1 H, CH₂CO), 2.450 (m, 1 H, CH₂CO), 3.001 (s, 3 H, N—CH₃), 3.350 (s, 3 H, OCH₃), 3.885 (brm, 1 H, CH—O), 4.774 (brm, 1 H, CH—N), 4.794 (dd, J=9.2, 6.5 Hz, 1 H, cal-S-CH), 6.875 (d, J=9.2 Hz, 1 H, val-NH), ¹³C NMR (CDCl₃)δ 10.71 (CH₃), 15.81 (CH₃), 17.87 (CH₃), 18.03 (CH₃), 19.77 (CH₃), 20.18 (CH₃), 25.76 (CH₂), 27.73 (CH), 28.14 (CH₃)₃, 30.99 (CH), 33.11 (N—CH₃), 38.58 (CH₂CO), 42.87 (N—(CH₃)₂), 53.73 (CH), 57.88 (OCH₃), 76.60 (CH), 78.27 (CH), 80.82 (qC), 171.12 (CO), 171.69 (CO), 173.3 (CO), and HRFABMS (m/z) 486.3906 ](M+H)+,90%, calcd. for C₂₆H₅₂N₃O₅: 486.3908], 100 (100%).

EXAMPLE 26

Dolastatin 10

To a cooled (0° C.) solution of Boc-S-Doe prepared according to Example 21 (23.3 mg, 0.077 mmol) in dichloromethane (1 ml) was added trifluoroacetic acid (0.4 ml). The solution was stirred at 0° C. for 1 hour, at room temperature for one hour, and the solvent was then evaporated in a stream of nitrogen. The residue was triturated with hexane and dried in a high vacuum over phosphorous pentoxide for 24 hours to afford the trifluoroacetate salt of dolaphenine as a viscous oil. A mixture of the trifluoroacetate salt (used without further purification) in dimethoxyethane (2 ml) and Boc-(2'R,3'R)-Dap of Example 15 (10 mg, 0.035 mmol) cooled to 0° C., was treated with triethylamine (0.022 ml, 0.15 mmol) followed by diethyl phosphorocyanidate (DEPC, 0.012 ml, 0.077 mmol). The mixture was stirred under argon for three hours at 0° C. Solvent was evaporated and the product was successively chromatographed on SEPHADEX$^R$ LH-20 in hexane-methanol-dichloromethane (2:2.5:7.5) followed by chromatography in a pipette filled with silica gel. Elution of the pipette column with hexane-acetone (9:1) yielded (8.8 mg, 50%) pure Boc-dipeptide as a viscous oil. The tripeptide ester S-Dov-S-Val-(3R, 4S,5S)-Dil-OBu$^t$ of Example 25 (46 mg) in dichloromethane (1 ml) was cooled to 0° C. and trifluoroacetic acid (0.5 ml) was added. After two hours under argon, the solvent was evaporated by a stream of nitrogen. Carbon tetrachloride was added and evaporated. The tripeptide trifluoroacetate salt was dried (vacuum desiccator, phosphorous pentoxide, overnight) to provide 48 mg (94%) for the next reaction (without further purification). Analogous treatment of Boc-(2S,2'R,3'R)-Dap-Doe (5.4 mg, 0.011 mmol) with trifluoroacetic acid (0.5 ml) in dichloromethane (0.5 ml) at 0° C. for one hour led to the corresponding dipeptide Tfa salt. A solution of this salt and that of the tripeptide carboxylic acid (7.4 mg, 0.014 mmol) in dimethoxyethane (0.5 ml) was cooled to 0° C. under argon. Triethylamine (0.008 ml, 0.057 mmol) was added followed by DEPC (0.003 ml, 0.02 mmol). The reaction mixture was stirred at 0° C. for an hour and at room temperature for two hours. After completion of peptide bond formation, the solvent was evaporated under a stream of nitrogen. The crude mixture was successfully chromatographed on a column of SEPHADEX® LH-20 in hexane-dichloromethane- methanol (2:7.5:2.5) followed by use of a pipette filled with silica gel. Gradient elution of the silica column with dichloromethane to dichloromethane-methanol (1→5%) gave the pentapeptide herein designated dolastatin 10 (6.6 mg, 74%) as an amorphous powder from acetone-hexane. The dolastatin 10 was accompanied by a trace of salt and/or a paramagnetic impurity. Therefore, it was dissolved in dimethoxyethane and treated with dilute ammonium hydroxide. After concentration to dryness and rechromatography, as described above on SEPHADEX® LH-20, silica gel and finally on SEPHADEX® LH-20 in methanol a pure sample was isolated that was found to be identical (TLC, $^1$H and $^{13}$C NMR, HPLC and $[\alpha]_D$) with natural dolastatin 10.

From the foregoing, it becomes apparent that new and useful procedures have been herein described and illustrated which fulfill all of the aforestated objectives in a remarkably unexpected fashion. It is of course understood that such modifications, alterations and adaptations as may readily occur to an artisan having the ordinary skills to which this invention pertains are intended within the spirit of the present invention which is limited only by the scope of the claims appended hereto.

Accordingly, what is claimed is:

1. The method of synthesizing dolastatin 10 comprising the steps of forming a solution of Z-(S,S)-isoleucine and methyl iodide in tetrahydrofuran; cooling said solution to about 0° C.; stirring said cooled solution under argon; adding sodium hydride to said stirred cooled solution to form a suspension; stirring said suspension at room temperature; adding ethyl acetate and ice water to said stirred suspension to form an aqueous layer; washing aqueous layer with ether; acidifying said washed aqueous layer with acid at 0° C.; extracting said acidified aqueous layer with ethyl acetate; and washing said extract; removing said solvent from said extract to provide N-Z-N-methyl- (S,S)- isoleucine; dissolving said N-Z-N-methyl-(S,S)- isoleucine in tetrahydrofuran at 0° C. under argon; adding borane-tetrahydrofuran complex to said solution with stirring; extracting the product from said solution with ethyl acetate; evaporating the solvent from extracted product to form an oil; filtering said oil through a column of silica gel; eluting said column with hexane-acetone (7:3) to form N-Z-N-methyl-(S,S)-isoleucinol; admixing said N-Z-N-methyl-(S,S)-isoleucinol with triethylamine in dimethylsulfoxide at room temperature; cooling the mixed solution to 0° C.; adding sulfur trioxide-pyridine complex to said solution under argon; extracting the aldehyde from said solution with ether; washing said ethereal solution successively with citric acid, water, and sodium bicarbonate to yield chromatographically pure N-Z-N-methyl- (S,S)-isoleucinal; preparing a solution of lithium diisopropylamide from n-butyllithium and diisopropylamine in tetrahydrofuran at −78° C.; warming said solution to −20° C.; recooling said solution to −78° C.; adding tert-butyl acetate to said recooled solution; stirring said solution while rewarming said solution to −20° C.; recooling said solution to −78° C. and adding said chromatographically pure N-Z-N-methyl-(S,S)-isoleucinal thereto; treating the resulting mixture with ice water; extracting the mixture with ether; drying said extract; solvent evaporating said dry extract to yield a viscous oil; chromatographing and eluting said viscous oil with hexane-acetone (47:3) to yield tert-butyl(3S,4S, 5S)-3-hydroxy-4-(N-Z-N-methyl)-amino-5-methyl-heptanoate and tert-butyl (3R,4S,5S)-3-hydroxy-4-(N-Z-N-methyl)-amino-5-methyl-heptanoate; adding boron trifluoride etherate to a cooled and stirred solution of tert-butyl (3R,4S,5S)-3-hydroxy-4-(N-Z-N-methyl) -amino-5-methyl-heptanoate in dichloromethane under argon; thereafter adding an anhydrous solution of diazomethane in dichloromethane to said solution; filtering the polymethylene side products from said solution to form a filtrate; concentrating said filtrate; chromatographing said concentrated filtrate on a silica gel column; eluting said column with hexane-acetone (97:3) to yield tert-butyl (3R,4S,5S)-3-methoxy-4-(N-Z-N-methyl) -amino-5-methyl-heptanoate; admixing trifluoroacetic anhydride in dichloromethane into a cooled −78° C. solution of dimethylsulfoxide in dichloromethane with stirring; adding N-Boc-S-prolinol in dichloromethane to said cool stirred mixture and continue stirring for about an hour; adding triethylamine to said solution; warming said solution to −20° C.; extracting said solution with ether to form an ethereal solution; washing and concentrating said ethereal solution to form an oil; dissolving said oil in acetone; filtering said oil-acetone solution through a silica-gel column; eluting said column with hexane-acetone (93:7) to yield N-Boc-S-prolinal; adding 2-S-Propionyloxy-1,1,2-triphenylethanol to a solution of lithium diisopropylamide in tetrahydrofuran at −78° C. under argon to form a reaction mixture; permitting said reaction mixture to warm to room temperature over two hours to form a yellow solution; cooling the yellow solution to −95° C.; adding freshly synthesized magnesium bromide to said cooled yellow solution; thereafter adding a solution of Boc-S-prolinal in tetrahydrofuran to said yellow solution and allowing the reaction therebetween to proceed for two hours at −95° C. under methanol-liquid nitrogen; terminating said reaction with saturated aqueous ammonium chloride; warming said mixture to 0° C.; adding ether to said mixture to form an ethereal solution; washing, drying and solvent evaporating said ethereal solution to provide a glassy solid; dissolving said glassy solid to form a solution; adsorbing said solution on silica gel; chromatographing said adsorbed silica gel; and eluting said chromatographed silica gel to provide N-Boc-2S-3'-[2"ethoxy-(1"hydroxy-1",1",2"-triphenyl) 2'S-methyl-3'R-hydroxy- propionate]-pyrrolidine; methylating said N-Boc-2S-3, propionate-pyrrolidine in dichloromethane with boron trifluoride etherate and diazomethane in anhydrous dichloromethane; eluting said methylated pyrrolidine with hexane-acetone (9:1) to provide N-Boc-2S-3'-[2'''-ethoxy(1''-hydroxy-1'',1'',2''-triphenyl) 2'S-methyl-3'R-methoxy-propionate]-pyrrolidine; adding potassium tert-butoxide to a solution of said (2'S,3'R) ester in tetrahydrofuran with stirring until the solution turns bright yellow; warming the bright yellow solution to −15° C. and stopping the epimerization thereof by the addition of sufficient saturated aqueous citric acid thereto to dilute said solution; extracting said solution with dichloromethane to form a combined extract; washing said extract and removing the solvent therefrom to provide a clear oil; chromatographing said yellow oil on silica gel; eluting said silica gel to provide N-Boc-2S-3'-[2''ethoxy(1''hydroxy- 1'',1'', 2''-triphenyl) 2'S- methyl-3'R-methoxy-propionate]-pyrrolidine; forming a solution of N-Boc-S-phenylalaninol in anhydrous dimethylsulfoxide-triethylamine; oxidizing said solution with sulfur trioxide pyridine complex; adding water to said oxidized solution to precipitate N-Boc-S-phenylalaninal; forming a solution of N-Boc-S-phenylalaninal and 2-aminoethanethiol in anhydrous benzene; stirring said solution under argon for four hours; removing the solvents and excess reagents from said stirred solution by filtration through a silica gel pad to form a residue; crystallizing said residue to form 2-(N-Boc-1'S-amino-2'-phenyl-ethyl)-2-(R,S)-thiazolidine [N-Boc-2(3),4(5)-tetrahydro-dolaphenine]; forming a suspension of battery grade manganese dioxide in anhydrous benzene; adding 1'-ethyl (N-Boc-1'S-amino-2'-phenyl)-2(R,S)-thiazolidine [N-Boc-2(3),4(5)-tetrahydro-dolaphenine] in benzene to said suspension to form a mixture; stirring said mixture under argon at 55° C. for 24 hours; adding additional manganese dioxide with continued stirring; filtering said stirred solution through silica gel; washing said silica gel sequentially with benzene, ethyl acetate, chloroform and chloroform acetone (1:1) to form a combined eluant; evaporating said combined eluant to form a residue; chromatographing said residue on a silica gel column; eluting said column with ethyl acetate-hexane; and crystallizing from said eluant granules consisting of 2-(1'S-Boc-amino-2'-phenyl-ethyl)-2-thiazole[N-Boc-S-dolaphenine].

2. The method of claim 1 in which said N-Z-N-methyl-(S,S)-isoleucine is prepared by the steps of forming a solution of Z-(S,S)-isoleucine and methyl iodide in tetrahydrofuran; cooling said solution to about 0° C.; stirring said cooled solution under argon; adding sodium hydride to said stirred cooled solution to form a suspension; stirring said suspension at room temperature; adding ethyl acetate and ice water to said stirred suspension to form an aqueous layer; washing said aqueous layer with ether; acidifying said washed aqueous layer with acid at 0° C.; extracting said acidified aqueous layer with ethyl acetate; and washing said extract; and removing said solvent from said extract to provide N-Z-N-methyl-(S,S)-isoleucine.

3. The method according to claim 2 including the further steps of dissolving said N-Z,N-methyl-(S,S)-isoleucine in tetrahydrofuran at 0° C. under argon; adding borane-tetrahydrofuran complex to said solution with stirring; extracting the product from said solution with ethyl acetate; evaporating the solvent from extracted product to form an oil; filtering said oil through a column of silica gel; and eluting said column with hexane-acetone (7:3) to form N-Z-N-methyl-(S,S)-isoleucinol.

4. The method of claim 1 in which said N,N-dimethyl-S-valine is prepared by the steps of forming a mixture of S-valine in water with formaldehyde and a catalyst; hydrogenating said mixture; heating said hydrogenated mixture at reflux; removing said catalyst from said heated hydrogenated mixture by filtration to form a filtrate; concentrating said filtrate in vacuo to create a residue; adding water and ethanol to said residue to form a solution; evaporating said solution to dryness; repeating the steps of adding water and ethanol and evaporating said solution to dryness until all paraformaldehyde is removed therefrom and an amorphous powder remains; admixing ethanol-acetone with said powder; and crystallizing colorless needles therefrom, said needles consisting of N,N-dimethyl-S-valine.

5. The method according to claim 1 comprising the further steps of: adding 5% Pd/C to a mixture of N-Z-dolaisoleuine tert-butyl ester in ethyl acetate-methanol (3:1); hydrogenating said mixture at ambient temperature and pressure; filtering the hydrogenated mixture to remove said Pd/C therefrom and create a filtrate; evaporating said filtrate to dryness; dissolving said dry filtrate in ether; cooling said solution to −60° C.; adding an ethereal solution of hydrogen chloride to said cooled solution under anhydrous conditions to precipitate a hydrochloride salt therefrom; passing argon into said mixture to remove excess hydrogen chloride therefrom; and collecting said hydrochloride salt consisting of Dolaisoleuine tert-butyl ester hydrochloride [Dil-OBu$^t$ HCl].

6. The method of claim 1 in which said N-Boc-S-prolinal is prepared by the steps of admixing triethylamine with a cooled solution of S-prolinol at 0° C. in dichloromethane; stirring said admixture; adding di-tert-butyldicarbonate to said cool stirred admixture with stirring; adding citric acid to said stirred mixture to form an organic layer; washing said organic layer with water; and removing the solvent from said washed organic layer to yield a clear oil consisting of N-Boc-S-prolinol.

7. The method of claim 1 in which Boc-(2S,2'R,3'R)-Dap is prepared by forming a mixture of the benzyl ester produced by claim 1 in ethyl acetate-methanol (3:1) and 10% Pd/C at ambient temperature; passing hydrogen through said mixture at ambient pressure for 48 hours; collecting said Pd/C catalyst on celite; washing said catalyst-containing celite with ethyl acetate to form a filtrate; evaporating said filtrate to form an oil; chromatographing said oil on a silica gel column; eluting said column with hexane-acetone (7:3) to form N-Boc-2S-3'-(2'S-methyl-3'R-methoxy-propionic acid)-pyrrolidine; [Boc-(2S,2'S,3'R)-Dap].

8. The method of claim 1 in which Boc-(2S,2'R,3'R)-Dap is prepared by forming a first solution of the (1'R,2'R)benzyl ester produced by claim 1 in methanol; forming a mixture of methanol and 10% Pd/C under nitrogen; adding said first solution to said mixture with stirring in a system to form a second solution; evacuating said system; flushing said system with hydrogen; removing said Pd/C catalyst from said second solution; removing the solvent from said second solution to form a glassy solid; dissolving said glassy solid in acetone; filtering said acetone solution through silica gel to form a filtrate; removing the solvent from said filtrate to form N-Boc-2S-3'-(2'R-methyl-3'R-methoxy-propionic acid) pyrrolidine; [Boc-(2S,2'R,3'R)-Dap].

9. The method of claim 1 in which said S-Dov-S-Val-oBu$^t$ is prepared by adding S-Val-OBu$^t$. hydrochloride to a solution of dolavaline in dimethylformamide to form a second solution; warming said second solution to effect dissolution; adding hydroxybenzotriazole and N-methylmorpholine to said warmed second solution to form a third solution; cooling said third solution to 0° C. over two hours; adding dicyclohexylcarbodiimide to said cooled third solution with stirring at room temperature for about fifteen hours to form a precipitate and a filtrate; separating said filtrate from said precipitate; concentrating said filtrate; adding said concentrated filtrate into ether to form an ethereal solution; washing said ethereal solution with aqueous sodium bicarbonate in cold water; solvent evaporating said washed ethereal solution to form a residue; chromatographing said residue on a flash column; and eluting said flash column with hexane-acetone (85:15) to isolate S-Dov-S-Val-OBu$^t$.

10. The method according to claim 9 including the following steps: forming a solution of S-Dov-S-Val-OBu$^t$ in dichloromethane-trifluoroacetic acid at 0° C.; stirring said solution at room temperature for one hour; evaporating the solvent from said solution; adding ethanol to said solvent evaporated solution; evaporating said ethanol-continuing solution to form a residue; adding ether-hexane to said residue; and crystallizing said residue from said ether-hexane to form S-Dov-S-Val.

11. The method of claim 1 in which said N-Z-S-Val-(3R,4S,5S)-Dil-OBu$^t$ is prepared by forming a solution of N-Z-S-valine in anhydrous chloroform at $-23°$ C.; adding to said solution under argon with stirring N-methylmorpholine followed by pivaloyl chloride to form a mixture; stirring said mixture at $-23°$ C. for three hours; adding (3R,4S,5S)-Dil-OBu$^t$.HCl and N-methyl morpholine to said stirred mixture with continuous stirring; concentrating said stirred mixture by sweeping with argon at room temperature; adding chloroform to said stirred solution; washing said chloroform containing solution sequentially with saturated aqueous citric acid, water, aqueous sodium bicarbonate and water; evaporating said washed solution to form a residue; chromatographing said residue on a silica gel column; and eluting said column with hexane-acetone to provide N-Z-S-Val-(3R,4S,5S)-Dil-OBu$^t$.

12. The method according to claim 4 including the steps of: forming a solution of dolavaline in pyridine; cooling said solution to 0° C.; adding pentafluorophenol trifluoroacetate and trifluoroacetic anhydride under argon to said stirred solution with stirring; adding ethyl acetate to said stirred solution to form an organic phase; washing said organic phase sequentially with aqueous sodium bicarbonate and water; solvent evaporating said washed solution to form an oil; purifying said oil by chromatography on a silica gel column; and eluting said column with hexane-acetone (99:1) to provide dolavaline pentafluorophenol ester.

13. The method of claim 12 including the steps of forming a solution of N-Z-(S)-Val-(3R,4S,5S)-Dil-OBu$^t$ and dolavaline pentafluorophenol ester in anhydrous dioxane; adding 10% Pd/C catalyst to said solution to form a mixture; saturating said mixture with hydrogen under anhydrous conditions and ambient temperature and pressure; filtering said hydrogenated mixture to remove said catalyst therefrom and provide a filtrate; evaporating the solvent from said filtrate to provide a residue; dissolving said residue in a benzene solvent to form a second solution; adding trifluoroacetic acid at 0° C. under argon to said second solution with stirring; removing said solvent from said second solution to leave a second residue; chromatographing said second residue on a SEPHADEX® LH-20 column in 3:2 dichloromethane-methanol; and isolating, by means of flash chromatography on a silica gel column with a hexane-acetone (4:1) eluant, a powder consisting of S-Dov-S-Val-(3R,4S,5S)-Dil-OBu$^t$.

14. The method of synthesizing dolastatin 10 comprising the steps of: forming a cooled first solution (0° C.) of 2-(N-Boc-1'S-amino-2'-phenyl-ethyl)-2-thiazole (N-Boc-S- dolaphenine), in dichloromethane; adding trifluoroacetic acid to said first solution to form a second solution; stirring said second solution at 0° C. for one hour and at room temperature for one hour; evaporating the solvent from said second solution in a stream of nitrogen to leave a residue; triturating said residue with hexane; drying said triturated residue in a high vacuum over phosphorous pentoxide for 24 hours to form the trifluoroacetate salt of dolaphenine as a gum; mixing said trifluoroacetate salt of dolaphenine in dimethoxyethane and Boc-(2S,2'R,3'R)-Dap to form a first mixture; cooling said mixture to 0° C.; treating said cooled first mixture with triethylamine followed by diethylphosphorocyanidate to form a second mixture; stirring said second mixture under argon for three hours at 0° C.; evaporating the solvent from said second mixture; chromatographing said second mixture successfully on SEPHADEX® LH-20 in hexane-methanol-dichloromethane (2:2.5:7.5) and on silica gel with hexane-acetone (9:1) to yield Boc-(2S,2'R,3'R)-Dap-Doe; concurrently therewith, forming a third solution of S-Dov-S-Val-(3R,4S,5S)-Dil-OBu$^t$ in dichloromethane; cooling said third solution to 0° C.; adding trifluoroacetic acid to said cooled third solution; holding said cooled third solution under argon for two hours; evaporating said third solution with a stream of nitrogen; adding carbon tetrachloride to said evaporated third solution; evaporating said carbon tetrachloride from said third solution to provide a tripeptide [S-Dov-S-Val-(3R,4S,5S)-Dil-OH] trifluoroacetic acid salt; drying said tripeptide trifluoroacetic acid salt; adding trifluoroacetic acid to said Boc-(2S,2'R,3'R)-Dap-S-Doe in dichloromethane at 0° C. to form a fourth solution; holding said fourth solution under argon for one hour; evaporating said fourth solution with a stream of nitrogen; adding carbon tetrachloride to said evaporated fourth solution; evaporating said carbon tetrachloride from said fourth solution to form a dipeptide trifluoroacetic acid salt; forming a fifth solution of said dipeptide [(2S,2'R,3'R)-Dap-S-Doe] trifluoroacetic acid salt and a trifluoroacetic acid salt of S-Dov-S-Val-(3R,4S,5S)-Dil in dimethoxyethane; cooling said fifth solution under argon to 0° C.; adding triethylamine and diethylphosphorocyanidate to said cooled fifth solution; stirring said fifth solution at 0° C. for one hour and then at room temperature for two hours to complete the peptide bond formation; evaporating the solvent from said fifth solution with a stream of nitrogen to form a crude mixture; chromatographing said crude mixture successfully on a column of SEPHADEX® LH-20 in hexane-dichloromethane- methanol (2:7.5:2.5) and on a column of silica gel; eluting said silica gel column with dichloromethane to dichloromethane-methanol gradient of from one to five percent to yield dolastatin 10 as an amorphous powder.

15. The method according to claim 14 including the further steps of dissolving said amorphous powder in dimethoxyethane to form a sixth solution; adding ammonium hydroxide to said sixth solution; concentrating said sixth solution to dryness; rechromatographing said dry solution successively on columns of SEPHADEX® LH-20, silica gel, and SEPHADEX® LH-20 in methanol to produce pure Dolastatin 10.

16. The method according to claim 6 including the steps of: dissolving N-Boc-S-prolinol in anhydrous dimethylsulfoxide at room temperature to form a solution; adding triethylamine to said solution to form a mixture; stirring said mixture at room temperature; cooling said stirred mixture to 0° C.; adding sulfur trioxide-pyridine complex to said cooled mixture with stirring at 0° C. for two hours; adding ice water to said mixture; pouring said iced mixture into water; extracted said water mixture with dichloromethane to form an extract; washing said extract sequentially with water, saturated aqueous citric acid, water, saturated aqueous sodium bicarbonate and water; drying said washed extract and removing the solvent therefrom to leave a residue; drying said residue under high vacuum to provide N-Boc-S-Prolinal as a yellow oil.

17. The method of claim 1 in which said 2-S-propionyloxy-1,1,2-triphenylethanol is prepared by forming a solution of 2S-hydroxy-1,1,2-triphenylethanol in pyridine; adding propionic anhydride to said solution to form a mixture; stirring said mixture to form a precipitate; filtering said mixture to collect said precipitate and form a filtrate; concentrating said filtrate by azeotropic distillation with pyridine to form a concentrate; and triturating said concentrate with methanol to form 2-S-propionyloxy-1,1,2-triphenylethanol.

18. The method of claim 1 in which said N-Boc-S-dolaphenine is prepared by forming a slurry of activated manganese dioxide with dry dioxane; introducing said slurry into a dry glass column; eluting said slurry containing glass column with dioxane under positive nitrogen pressure; flowing N-Boc-2(3),4(5)-tetrahydro-dolaphenine in dry dioxane through said column for four hours; discarding the initial fraction from said column; collecting all subsequent fractions and recovering N-Boc-S-dolaphenine therefrom.

19. The method of claim 14 in which said N-Boc-S-dolaphine is prepared by forming a solution of N-Boc-S-Phenylalaninol in anhydrous dimethylsulfoxide-triethylamine; oxidizing said solution with sulfur trioxide pyridine complex; adding water to said oxidized solution to precipitate N-Boc-S-phenylalaninol; forming a solution of said N-Boc-S-phenylalaninal and 2-aminoethanethiol in anhydrous benzene; stirring said solution under argon for four hours; removing the solvents and excess reagents from said stirred solution by filtration through a silica gel pad to form a residue; crystallizing said residue to form 2-(N-Boc-1'S-amino-2'-phenyl-ethyl)-2-(R,S)-thiazolidine [N-Boc-2(3),4(5)-tetrahydro-dolaphenine]; forming a suspension of battery grade manganese dioxide in anhydrous benzene; adding 1'-ethyl (N-Boc-1'S-amino-2'-phenyl)-2 (R,S)-thiazolidine [N-Boc-2(3),4(5)-tetrahydro-dolaphenine] in benzene to said suspension to form a mixture; stirring said mixture under argon at 55° C. for 24 hours; adding additional manganese dioxide with continued stirring; filtering said stirred solution through silica gel; washing said silica gel sequentially with benzene, ethyl acetate, chloroform and chloroform acetone (1:1) to form a combined eluant; evaporating said combined eluant to form a residue; chromatographing said residue on a silica gel column; eluting said column with ethyl acetate-hexane; and crystallizing from said eluant granules consisting of 2-(1'S-Boc-amino-2'-phenyl-ethyl)-2-thiazole [N-Boc-S-dolaphenine].

20. The method of claim 14 in which said Boc-(2S,2'R,3R)-Dap is prepared by admixing trifluoroacetic anhydride in dichloromethane into a cooled −78° C. solution of dimethylsulfoxide in dichloromethane with stirring; adding N-Boc-S-prolinol in dichloromethane to said cool stirred mixture and continue stirring for about an hour; adding triethylamine to said solution; warming said solution to −20° C.; extracting said solution with ether to form an ethereal solution; washing and concentrating said ethereal solution to form an oil; dissolving said oil in acetone; filtering said oil-acetone solution through a silica-gel column; eluting said column with hexane-acetone (93:7) to yield N-Boc-S-prolinal; adding 2S-Propionyloxy-1,1,2-triphenylethanol to a solution of lithium diisopropylamide in tetrahydrofuran at −78° C. under argon to form a reaction mixture; permitting said reaction mixture to warm to room temperature over two hours to form a yellow solution; cooling the yellow solution to −95° C.; adding freshly synthesized magnesium bromide to said cooled yellow solution; thereafter adding a solution of Boc-S-prolinal in tetrahydrofuran to said yellow solution and allowing the reaction therebetween to proceed for two hours at −95° C. under methanol-liquid nitrogen; terminating said reaction with saturated aqueous ammonium chloride; warming said mixture to 0° C.; adding ether to said mixture to form an ethereal solution; washing, drying and solvent evaporating said ethereal solution to provide a glassy solid; dissolving said glassy solid to form a solution; adsorbing said solution on silica gel; chromatographing said adsorbed silica gel; eluting said chromatographed silica gel to provide N-Boc-2S-3'-[2''-ethoxy-(1''-hydroxy-1'',1'',2''-triphenyl) 2'S-methyl-3'R-hydroxy-propionate]-pyrrolidine; methylating said N-Boc-2S-3' propionate-pyrrolidine in dichloromethane with boron trifluoride etherate and diazomethane in anhydrous dichloromethane; eluting said methylated pyrrolidine with hexane-acetone (9:1) to provide N-Boc-2S-3'-[2''-ethoxy(1''-hydroxy-1'',1'',2''-triphenyl) 2'S-methyl-3'R-methoxy-propionate]-pyrrolidine; adding potassium tert-butoxide to a solution of said (2'S,3'R) ester in tetrahydrofuran with stirring until the solution turns bright yellow; warming the bright yellow solution to −15° C. and stopping the epimerization thereof by the addition of sufficient saturated aqueous citric acid thereto to dilute said solution; extracting said solution with dichloromethane to form a combined extract; washing said extract and removing the solvent therefrom to provide a clear yellow oil; chromatographing said yellow oil on silica gel; eluting said silica gel to provide N-Boc-2S-3'-[2''ethoxy(1''-hydroxy-1'',1'',2''-triphenyl) 2'S- methyl-3'R-methoxy-propionate] -pyrrolidine.

21. The method of claim 14 in which said S-Dov-S-Val-(3R,4S,5S)-Dil-OBu$^t$ is prepared by admixing said N-Z-N-methyl-(S,S)- isoleucinol with triethylamine in dimethylsulfoxide at room temperature; cooling the mixed solution to 0° C.; adding sulfur trioxide-pyridine complex to said solution under argon; extracting the aldehyde from said solution with ether; washing said ethereal solution successively with citric acid, water, and sodium bicarbonate to yield chromatographing pure N-Z-N-methyl-(S,S)-isoleucinal; preparing a solution of lithium diisopropylamide from n-butyllithium and diisopropylamine in tetrahydrofuran at −78° C.; warming said solution to −20° C.; recooling said solution to −78° C.; adding tert-butyl acetate to said recooled solution; stirring said solution while rewarming said solution to −20° C.; recooling said solution to −78° C. and adding said chromatographically pure N-Z-N-methyl-(S,S)-isoleucinal thereto; treating the resulting mixture with ice water; extracting the mixture with ether; drying said extract; solvent evaporating said dry extract to yield a viscous oil; chromatographing and eluting said viscous oil with hexane-acetone (47:3) to yield tert-butyl(3S,4S, 5S)-3-hydroxy-4-(N,Z-N-methyl)-amino-5-methyl-heptanoate and tert-butyl (3R,4S,5S)-3- hydroxy-4-(N-Z-N-methyl)-amino-5-methyl-heptanoate; adding boron trifluoride etherate to a cooled and stirred solution of tert-butyl (3R,4S,5S)-3-hydroxy-4-(N-Z-N-methyl)-amino-5-methyl-heptanoate in dichloromethane under argon; thereafter adding an anhydrous solution of diazomethane in dichloromethane to said solution; filtering the polymethylene side products from said solution to form a filtrate; concentrating said filtrate; chromatographing said concentrated filtrate on a silica gel column; eluting said column with hexane-acetone (97:3) to yield tert-butyl (3R,4S,5S)-3- methoxy-4-(N-Z-N-methyl)-amino-5-methyl-heptanoate.

22. The method of claim 19 in which said Boc-(2S,2′R,3′R)-Dap is prepared by admixing trifluoroacetic anhydride in dichloromethane into a cooled −78° C. solution of dimethylsulfoxide in dichloromethane with stirring; adding N-Boc-S-prolinol in dichloromethane to said cool stirred mixture and continue stirring for about an hour; adding triethylamine to said solution; warming said solution to −20° C.; extracting said solution with ether to form an ethereal solution; washing and concentrating said ethereal solution to form an oil; dissolving said oil in acetone; filtering said oil-acetone solution through a silica-gel column; eluting said column with hexane-acetone (93:7) to yield N-Boc-S-prolinal; adding 2S-Propionyloxy-1,1,2-triphenylethanol to a solution of lithium diisopropylamide in tetrahydrofuran at −78° C. under argon to form a reaction mixture; permitting said reaction mixture to warm to room temperature over two hours to form a yellow solution; cooling the yellow solution to −95° C.; adding freshly synthesized magnesium bromide to said cooled yellow solution; thereafter adding a solution of Boc-S-prolinal in tetrahydrofuran to said yellow solution and allowing the reaction therebetween to proceed for two hours at −95° C. under methanol-liquid nitrogen; terminating said reaction with saturated aqueous ammonium chloride; warming said mixture to 0° C.; adding ether to said mixture to form an ethereal solution; washing, drying and solvent evaporating said ethereal solution to provide a glassy solid; dissolving said glassy solid to form a solution; adsorbing said solution on silica gel; chromatographing said adsorbed silica gel; eluting said chromatographed silica gel to provide N-Boc-2S-3′-[2″-ethoxy-(1″-hydroxy-1″,1″,2″-triphenyl) 2′S-methyl-3′R-hydroxy-propionate]-pyrrolidine; methylating said N-Boc-2S-3′ propionate-pyrrolidine in dichloromethane with boron trifluoride etherate and diazomethane in anhydrous dichloromethane; eluting said methylated pyrrolidine with hexane-acetone (9:1) to provide N-Boc-2S-3′-[2″-ethoxy(1″-hydroxy-1″,1″,2″-triphenyl) 2′S-methyl-3′R-methoxy-propionate]-pyrrolidine; adding potassium tert-butoxide to a solution of said (2′S,3′R) ester in tetrahydrofuran with stirring until the solution turns bright yellow; warming the bright yellow solution to −15° C. and stopping the epimerization thereof by the addition of sufficient saturated aqueous citric acid thereto to dilute said solution; extracting said solution with dichloromethane to form a combined extract; washing said extract and removing the solvent therefrom to provide a clear yellow oil; chromatographing said yellow oil on silica gel; eluting said silica gel to provide N-Boc-2S-3′[2″ethoxy(1″-hydroxy-1″,1″,2″-triphenyl) 2′S-methyl-3′R-methoxy-propionate]-pyrrolidine.

23. The method of claim 19 in which said S-Dov-S-Val-(3R,4S,5S)-Dil-OBu$^t$ is prepared by admixing said N-Z-N-methyl-(S,S)- isoleucinol with triethylamine in dimethylsulfoxide at room temperature; cooling the mixed solution to 0° C.; adding sulfur trioxide-pyridine complex to said solution under argon; extracting the aldehyde from said solution with ether; washing said ethereal solution successively with citric acid, water, and sodium bicarbonate to yield chormatographically pure N-Z-N-methyl-(S,S)-isoleucinal; preparing a solution of lithium diisopropylamide from n-butyllithium and diisopropylamine in tetrahydrofuran at −78° C.; warming said solution to −20° C.; recooling said solution to −78° C.; adding tert-butyl acetate to said recooled solution; stirring said solution while rewarming said solution to −20° C.; recooling said solution to −78° C. and adding said chromatographically pure N-Z-N-methyl-(S,S)-isoleucinal thereto; treating the resulting mixture with ice water; extracting the mixture with ether; drying said extract; solvent evaporating said dry extract to yield a viscous oil; chromatographing and eluting said viscous oil with hexane-acetone (47:3) to yield tert-butyl(3S,4S,5S)-3-hydroxy-4-(N-Z-N-methyl)-amino-5-methyl-heptanoate and tert-butyl (3R,4S,5S)-3-hydroxy-4-(N-Z-N-methyl)amino-5-methyl-heptanoate; adding boron trifluoride etherate to a cooled and stirred solution of tert-butyl (3R,4S,5S)-3-hydroxy-4-(N-Z-N-methyl)amino-5-methyl-heptanoate in dichloromethane under argon; thereafter adding an anhydrous solution of diazomethane in dichloromethane to said solution; filtering the polymethylene side products from said solution to form a filtrate; concentrating said filtrate; chromatographing said concentrated filtrate on a silica gel column; eluting said column with hexane-acetone (97:3) to yield tert-butyl (3R,4S,5S)-3-methoxy-4-(N-Z-N-methyl)-amino-5-methyl-heptanoate [N-Z-Dolaisoleuine tert-butyl ester].

24. The method of claim 20 in which said S-Dov-S-Val-(3R,4S,5S)-Dil-OBu$^t$ is prepared by admixing said N-Z-N-methyl-(S,S)-isoleucinol with triethylamine in dimethylsulfoxide at room temperature; cooling the mixed solution to 0° C.; adding sulfur trioxide-pyridine complex to said solution under argon; extracting the aldehyde from said solution with ether; washing said ethereal solution successively with citric acid, water, and sodium bicarbonate to yield chromatographically pure N-Z-N-methyl-(S,S)-isoleucinal; preparing a solution of lithium diisopropylamide from n-butyllithium and diisopropylamine in tetrahydrofuran at −78° C.; warming said solution to −20° C.; recooling said solution to −78° C.; adding tert-butyl acetate to said recooled solution; stirring said solution while rewarming said solution to −20° C.; recooling said solution to −78° C. and adding said chormatographically pure N-Z-N-methyl-(S,S)- isoleucinal thereto; treating the resulting mixture ether; drying said extract; solvent evaporating said dry extract to yield a viscous oil; chromatographing and eluting said viscous oil with hexane-acetone (47:3) to yield tert-butyl(3S,4S, 5S)-3- hydroxy-4-(N-Z-N-methyl)-amino-5-methyl-heptanoate and tert-butyl (3R,4S,5S)-3-hydroxy-4-(N-Z-N-methyl)-amino-5-methyl-heptanoate; adding boron trifluoride etherate to a cooled and stirred solution of tert-butyl (3R,4S,5S)-3-hydroxy-4-(N-Z-N-methyl)-amino-5-methyl-heptanoate in dichloromethane under argon; thereafter adding an anhydrous solution of diazomethane in dichloromethane to said solution; filtering the polymethylene side products from said solution to form a filtrate; concentrating said filtrate; chromatographing said concentrated filtrate on a silica gel column; eluting said column with hexane-acetone (97:3) to yield tert-butyl (3R,4S,5S)-3-methoxy-4-(N-Z-N-methyl)-amino-5-methyl-heptanoate.

* * * * *